(12) United States Patent
Julius et al.

(10) Patent No.: US 7,592,310 B2
(45) Date of Patent: Sep. 22, 2009

(54) INDUCTION OF ANTIBIOTIC PROTEINS AND PEPTIDES BY LAIT/SCD14-PROTEIN

(75) Inventors: Michael H. Julius, Toronto (CA); Dominik Filipp, Woodbridge (CA)

(73) Assignee: Gemma Biotechnology Ltd., Toronto (CA)

( * ) Notice: Subject to any disclaimer, the term of this patent is extended or adjusted under 35 U.S.C. 154(b) by 466 days.

(21) Appl. No.: 10/891,105

(22) Filed: Jul. 15, 2004

(65) Prior Publication Data

US 2004/0259795 A1 Dec. 23, 2004

Related U.S. Application Data

(63) Continuation of application No. 09/721,904, filed on Nov. 27, 2000, now abandoned, which is a continuation of application No. PCT/CA99/00482, filed on May 27, 1999.

(60) Provisional application No. 60/086,884, filed on May 27, 1998.

(51) Int. Cl.
*A61K 38/17* (2006.01)
(52) U.S. Cl. ..................... 514/12; 424/185.1
(58) Field of Classification Search ........................ None
See application file for complete search history.

(56) References Cited

U.S. PATENT DOCUMENTS

| | | | |
|---|---|---|---|
| 5,543,303 | A | 8/1996 | Goyert |
| 5,714,469 | A | 2/1998 | DeMarsh |
| 5,730,980 | A | 3/1998 | Ulevitch et al. |
| 5,804,189 | A | 9/1998 | Goyert |
| 5,820,858 | A | 10/1998 | Leturcq et al. |
| 5,869,055 | A | 2/1999 | Juan et al. |
| 6,093,693 | A * | 7/2000 | Julius et al. ............. 514/8 |
| 6,248,329 | B1 | 6/2001 | Chandrashekar et al. |

FOREIGN PATENT DOCUMENTS

| | | |
|---|---|---|
| WO | 9319772 A | 10/1993 |
| WO | 9534289 | 12/1995 |
| WO | 9632418X | 10/1996 |
| WO | 9620957 A | 11/1996 |
| WO | 9814473 A | 4/1998 |
| WO | 9822580 A | 5/1998 |

OTHER PUBLICATIONS

Diamond et al., Proc. Natl. Acad. Sci., 1996, vol. 93, pp. 5156-5160.*
Diamond G. et al. "Inducible Expression of an Antibiotic Peptide Gene in Lipopolysaccharide-challenged . . . ", Proc. Natl. Acad. Sci. USA, 93:5156-5160, May 1996 XP002127991.
Ferrero E. et al. "Transgenic Mice Expressing Human CD14 are Hypersensitive to Lipoplysaccharide" Proc. Natl. Acad. Sci. USA, 90:2380-2384, Mar. 1993 XP002016890.
Ikeda A. et al. "Molecular Cloning of Bovine CD14 Gene", Journal of Veterinary Medical Science-Nihon Juigaku Zasshi, JP, 59(8):715-719, 1997 XP002062359, Tokyo, JP.
Wang, Y. et al. "Detection and Identification of Soluble CD14 Bovine Milk", Molecular Biology of the Cell, Abstract, 1997, XP002062360, Bethesda, MD, USA.
Goyert, S.M. et al. "expression and Function of Human CD14 in Transgenic Mice", Journal of Cellular Biochemistry, 16C:153, Abstract, 1992, XP002016892, NY, USA.
Yang Z. et al. "Soluble CD14 and Lipopolysaccharide-Binding Protein From Bovine Serum Enable Bacteria . . . ", Journal of Leukocyte Biology, 59(2):241-247, 1996 XP002062361.
Simmons D.L. et al. "Monocyte Antigen CD14 is a Phospholipid Anchored Membrane Protein", 73(1):284-289, Jan. 1989, XP002062358, Philadelphia, PA, USA.
Setoguchi M. et al. "Mouse and Human CD14 (Myeloid Cell-Specific Leucine-Rich Glycoprotein) Primary . . . ", Biochemica et Biophysica Acta., 1008:213-222, 1989, XP002062356.
Ulevitch, R.J. et al. "Receotir-Dependent Mechanisms of Cell Stimulation By Bacterial Endotoxin", Annual Review of Immunology, 13:437-457, 1995, XP002071335 ISSN: 0732-0582.
Loms et al. CD14 is Expressed and Functional in Human B Cekks:m European Journal of Immunology, 24(8):1937-1940, 1994 XP002071627 ISSN: 0014-2980.
Yang et al. "Analysis of the CD14 Receptor Associated with Bovine Alveolar Macrophages" Inflammation, 20(1):97-106, Feb. 1996 XP002062355 ISSN: 0360-3997.
Jabara, et al. "Engagement of CD14 on Monocytes inhibits the Synthesis of Human lgs Including IgE", The Journal of Immunology, 153:972-978, 1994 XP002062357 ISSN: 0022-1767.
Juan, et al. "Soluble CD14 Truncated at Amino Acid 152 Binds Lipopolysaccharide (LPS) and Enables Cellular . . . ", The Journal of Biological Chemistry, 270:1382-1387, 1995.
Viriyakosol et al. "The N-Terminal Half of Membrane CD14 is a Functional Cellular Lipopolysaccharide Receptor", Infection and Immunity, 642(2):653-656, Feb. 1996.

(Continued)

*Primary Examiner*—Christopher R. Tate
*Assistant Examiner*—Roy Teller
(74) *Attorney, Agent, or Firm*—Torys LLP

(57) ABSTRACT

A method of ameliorating the symptoms of sepsis comprising directly exposing epithelial cells of a mammal in need thereof to soluble CD14, or active variants thereof. A method of obtaining CD14 from a stock solution containing protein of a mammary secretion is described. A method of directly activating B cells using a soluble polypeptide having the amino acid sequence selected from the group consisting of leu-leu-leu-leu-leu-leu-pro-ser, leu-leu-leu-leu-leu-leu-pro-leu; and leu-leu-leu-leu-leu-leu-val-his, and which is specifically recognized by the monoclonal antibody 3C10 and which activates B cells is described. Bovine CD14 genomic DNA is described.

22 Claims, 10 Drawing Sheets

OTHER PUBLICATIONS

Julius et al. "A Colostral Protein that Induces the Growth and Differentiation of Resting B Lymphocytes" The Journal of Immunology, 140(5):1366-1371, Mar. 1, 1987.

Filipp et al. "Soluble CD14 Enriched in Colostrum and Milk Induces B Cell Growth and Differentiation", PNAS, 98 (2):603-608, Jan. 16, 2001.

International Search Report, issued on International Patent Application No. PCT/CA 1999/00482 and published Apr. 6, 2000 under WO 99/61468.

International Search Report, issued on International Patent Application No. PCT CA 1997/00880 and published on Oct. 1, 1998 under WO 98/22580.

Landmann et al. "Soluble CD14 Activates Monocytic Cells Independently of Lipopolysaccharide", Infection and Immunity, 66(5):2264-2271, May 1998, XP000882503.

Sundan et al. "Soluble CD14 From Urine Copurifies with a Potent Inducer of Cytokines", European Journal of Immunology, 24:1779-1784, 1994 XP000882498.

Ferrero et al. "Nucleotide Sequence of the Gene Encoding the Monocyte . . . ", Nucleic Acids Rsch., GB, Oxford University Press, 16(9):4173, 1988, XP002916988 ISSN: 0305-1048.

Zhou et al. PNAS (1998) 95:2492-7.

Whisstock et al. "Prediction of Protein Function From Protein Sequence and Structure", Quarterly Review of Biophysics, 2003, 36 pp. 307-340.

Attwood, T., "The Babel of Bioinformatics", Science 2000, 290:471-473.

Skolnick et al. "Trends in Biotech 2000", 18(1):34-39.

Metzler et al. "Nature Structural Biol.", 1997, 4:527-531.

Janeway, C.A. et al. "The Immune System in Health and Disease", Immunobiology, Third Edition, Chapter 13.

Ellis, R.W. (Chapter 29 of "Vaccines", Plotkin, S.A. et al., 1988, pp. 568-574.

Ezzell, The Journal of NIH Research, "Cancer 'Vaccines': An Idea Whose Time Has Come?", 1995, vol. 7, pp. 46-49.

Database EMBL-EBI Bos Taurus CD14 mRNA, partial CDs., Sep. 13, 1996, Database Accession No. U48356.

Saha K. et al., "Use of Human Colostrum in the Management of Chronic Infantile Diarrhoea due to Enteropathogenic *E. coli* Infection with Associated Intestinal Parasite Infestations and Undernutrition". Journal of Tropical Pediatrice (1990). vol. 36, pp. 247-250.

Seifert E., "Human milk as prevention of intestinal infections in the newborns". Kinderkrankenschwester (1995), vol. 14, No. 12, p. 503.

L.A. Hanson and J. Winberg, "Breast Milk and Defence against Infection in the Newborn". Archives of Disease in Childhood (1972), vol. 47, pp. 845-847.

European Examination Report for EP 99 923 333.1-2405, dated Nov. 6, 2008.

* cited by examiner

No Stimulus     LPS (10μg/ml)     rBo-LAIT (0.3μg/ml)

Figure 8A

TAP286a:

5'-GCT CTG TCA AAG GGG GCA GTT TCT GAC TGG GCA TTG A-3'

TAP48a:

5'- CCA AGC AGA CAG GAC CAG GAA GAG GAG CGC GAG GAG CAG GTG ATG GAG CCT CAT-3'

Figure 8B

Tub-1:

5'-GAG TCG TCT CCT CCC CCA TAT GTC TTG TC-3'

SEQUENCE LISTING

<160> NUMBER OF SEQ ID NOS: 11

<210> SEQ ID NO 1
<211> LENGTH: 1122
<212> TYPE: DNA
<213> ORGANISM: bovine

<400> SEQUENCE: 1

| | | | | | |
|---|---|---|---|---|---|
| atggtgtgcg | tgccctacct | gctgctgctg | ctgctgccgt | cactgctgcg | tgtgtctgcg | 60 |
| gacacaacag | aaccctgcga | gctggacgac | gacgatttcc | gttgtgtctg | caacttcacg | 120 |
| gatccgaagc | ctgactggtc | tagcgccgtt | cagtgtatgg | ttgccgtcga | ggtggagatc | 180 |
| agtgccggcg | gccgcagcct | ggaacagttt | ctcaagggag | ccgacaccaa | cccgaagcag | 240 |
| tatgctgaca | caatcaaggc | tctgcgcgtt | cggcgactca | agctgggcgc | tgcacaggtt | 300 |
| cctgctcagc | ttctggtcgc | cgttctgcgc | gcgctcgggt | actctcgtct | caaggaactg | 360 |
| acgcttgagg | acctggaggt | aaccggccca | cgcccccga | cgcctctgga | agccgctggg | 420 |
| cctgcgctca | ccaccctcag | tctgcgtaac | gtatcgtgga | caacaggagg | tgcctggctc | 480 |
| ggcgaactgc | agcagtggct | caagcctggg | ctcagggtgc | tgaacattgc | ccaagcacac | 540 |
| tcgcttgcct | ttccgtgcgc | agggctctcc | accttcgagg | cgctcaccac | cctagacctg | 600 |
| tctgacaatc | ccagtctcgg | cgacacgggg | ctgatggcag | ctctctgtcc | gaacaagttc | 660 |
| ccggccctcc | aatatctagc | gctacgcaac | gcggggatgg | agacgccgag | cggcgtgtgc | 720 |
| gcggcgctgg | cggcagcgag | ggtgcagccc | caaagcctgg | acctcagcca | caactcgctg | 780 |
| cgcgtcaccg | ccccgggtgc | tacccgatgt | gtctggccca | gtgcactaag | gtctctcaat | 840 |
| ttgtcgttcg | ctgggctgga | gcaagtgcct | aagggactgc | ccctaagct | cagcgtgctt | 900 |
| gatctcagct | gcaacaagct | aagcaggag | ccgcggcgag | acgagctgcc | cgaggtaaat | 960 |
| gacctgactc | tggacggaaa | tcccttctg | gaccctggag | ccctccagca | ccaaaatgac | 1020 |
| ccgatgatct | ccggcgtggt | cccagcctgt | gcgcgttctg | ccttgaccat | ggggtgtca | 1080 |
| ggagccctgg | cgctgcttca | aggagcccga | ggcttcgcgt | aa | | 1122 |

<210> SEQ ID NO 2
<211> LENGTH: 1128
<212> TYPE: DNA
<213> ORGANISM: human

<400> SEQUENCE: 2

| | | | | | |
|---|---|---|---|---|---|
| atggagcgcg | cgtcctgctt | gttgctgctg | ctgctgccgc | tggtgcacgt | ctctgcgacc | 60 |
| acgccagaac | cttgtgagct | ggacgatgaa | gatttccgct | gcgtctgcaa | cttctccgaa | 120 |
| cctcagcccg | actggtccga | agccttccag | tgtgtgtctg | cagtagaggt | ggagatccat | 180 |
| gccggcggtc | tcaacctaga | gccgtttcta | aagcgcgtcg | atgcggacgc | cgacccgcgg | 240 |
| cagtatgctg | acacggtcaa | ggctctccgc | gtgcggcggc | tcacagtggg | agccgcacag | 300 |
| gttcctgctc | agctactggt | aggcgccctg | cgtgtgctag | cgtactcccg | cctcaaggaa | 360 |
| ctgacgctcg | aggacctaaa | gataaccggc | accatgcctc | cgctgcctct | ggaagccaca | 420 |
| ggacttgcac | tttccagctt | gcgcctacg | aacgtgtcgt | gggcgacagg | gcgttcttgg | 480 |
| ctcgccgagc | tgcagcagtg | gctcaagcca | ggcctcaagg | tactgagcat | tgcccaagca | 540 |
| cactcgcctg | ccttttcctg | cgaacaggtt | cgcgccttcc | cggcccttac | cagcctagac | 600 |
| ctgtctgaca | atcctggact | gggcgaacgc | ggactgatgg | cggctctctg | tccccacaag | 660 |

```
ttcccggcca tccagaatct agcgctgcgc aacacaggaa tggagacgcc cacaggcgtg    720
tgcgccgcac tggcggcggc aggtgtgcag ccccacagcc tagacctcag ccacaactcg    780
ctgcgcgcca ccgtaaaccc tagcgctccg agatgcatgt ggtccagcgc cctgaactcc    840
ctcaatctgt cgttcgctgg gctggaacag gtgcctaaag gactgccagc caagctcaga    900
gtgctcgatc tcagctgcaa cagactgaac agggcgccgc agcctgacga gctgcccgag    960
gtggataacc tgacactgga cgggaatccc ttcctggtcc ctggaactgc cctcccccac   1020
gagggctcaa tgaactccgg cgtggtccca gcctgtgcac gttcgaccct gtcggtgggg   1080
gtgtcgggaa ccctggtgct gctccaaggg gcccggggct tgcctaa               1128

<210> SEQ ID NO 3
<211> LENGTH: 1101
<212> TYPE: DNA
<213> ORGANISM: murine

<400> SEQUENCE: 3
atggagcgtg tgcttggctt gttgctgttg cttctggtgc acgcctctcc cgccccacca     60
gagccctgcg agctagacga ggaaagttgt tcctgcaact ctcagatccc gaagccagat    120
tggtccagcg ctttcaattg tttgggggcg gcagatgtgg aattgtacgg cggcggccgc    180
agcctggaat accttctaaa gcgtgtggac acggaagcag atctgggggca gttcactgat    240 attatcaagt ctctgtcctt aaagcggctt acggtgcggg ccgcgcggat tcctagtcgg    300
attctattcg gagccctgcg tgtgctcggg atttccggcc tccaggaact gactcttgaa    360
aatctcgagg taaccggcac cgcgccgcca ccgcttctgg aagccaccgg acccgatctc    420
aacatcttga acctccgcaa cgtgtcgtgg caacaaggg atgcctggct cgcagaactg    480
cagcagtggc taaagcctgg actcaaggta ctgagtattg cccaagcaca ctcactcaac    540
ttttcctgcg aacaggtccg cgtcttccct gccctctcca ccttagacct gtctgacaat    600
cctgaattgg gcgagagagg actgatctca gccctctgtc ccctcaagtt cccgaccctc    660
caagttttag cgctgcgtaa cgcggggatg agacgcccca gcggcgtgtg ctctgcgctg    720
gccgcagcaa gggtacagct gcaaggacta gaccttagtc acaattcact gcgggatgct    780
gcaggcgctc cgagttgtga ctggcccagt cagctaaact cgctcaatct gtcttcact    840 gggctgaagc aggtacctaa agggctgcca gccaagctca gcgtgctgga tctcagttac    900
aacaggctgg ataggaaccc tagcccagat gagctgcccc aagtggggaa cctgtcactt    960
aaaggaaatc cctttttgga ctctgaatcc cactcggaga gtttaactc tggcgtagtc   1020 accgccggag ctccatcatc ccaagcagtg gccttgtcag gaactctggc tttgctccta   1080
ggagatcgcc tctttgttta a                                             1101

<210> SEQ ID NO 4
<211> LENGTH: 373
<212> TYPE: PRT
<213> ORGANISM: bovine

<400> SEQUENCE: 4

Met Val Cys Val Pro Tyr Leu Leu Leu Leu Leu Pro Ser Leu Leu
1               5                   10                  15

Arg Val Ser Ala Asp Thr Thr Glu Pro Cys Glu Leu Asp Asp Asp
            20                  25                  30

Phe Arg Cys Val Cys Asn Phe Thr Asp Pro Lys Pro Asp Trp Ser Ser
        35                  40                  45
```

Ala Val Gln Cys Met Val Ala Val Glu Val Glu Ile Ser Ala Gly Gly
 50                  55                  60

Arg Ser Leu Glu Gln Phe Leu Lys Gly Ala Asp Thr Asn Pro Lys Gln
65                  70                  75                  80

Tyr Ala Asp Thr Ile Lys Ala Leu Arg Val Arg Arg Leu Lys Leu Gly
                85                  90                  95

Ala Ala Gln Val Pro Ala Gln Leu Leu Ala Val Leu Arg Ala Leu
            100                 105                 110

Gly Tyr Ser Arg Leu Lys Glu Leu Thr Leu Glu Asp Leu Glu Val Thr
        115                 120                 125

Gly Pro Thr Pro Pro Thr Pro Leu Glu Ala Ala Gly Pro Ala Leu Thr
    130                 135                 140

Thr Leu Ser Leu Arg Asn Val Ser Trp Thr Thr Gly Gly Ala Trp Leu
145                 150                 155                 160

Gly Glu Leu Gln Gln Trp Leu Lys Pro Gly Leu Arg Val Leu Asn Ile
                165                 170                 175

Ala Gln Ala His Ser Leu Ala Phe Pro Cys Ala Gly Leu Ser Thr Phe
            180                 185                 190

Glu Ala Leu Thr Thr Leu Asp Leu Ser Asp Asn Pro Ser Leu Gly Asp
        195                 200                 205

Thr Gly Leu Met Ala Ala Leu Cys Pro Asn Lys Phe Pro Ala Leu Gln
    210                 215                 220

Tyr Leu Ala Leu Arg Asn Ala Gly Met Glu Thr Pro Ser Gly Val Cys
225                 230                 235                 240

Ala Ala Leu Ala Ala Ala Arg Val Gln Pro Gln Ser Leu Asp Leu Ser
                245                 250                 255

His Asn Ser Leu Arg Val Thr Ala Pro Gly Ala Thr Arg Cys Val Trp
            260                 265                 270

Pro Ser Ala Leu Arg Ser Leu Asn Leu Ser Phe Ala Gly Leu Glu Gln
        275                 280                 285

Val Pro Lys Gly Leu Pro Pro Lys Leu Ser Val Leu Asp Leu Ser Cys
    290                 295                 300

Asn Lys Leu Ser Arg Glu Pro Arg Arg Asp Glu Leu Pro Glu Val Asn
305                 310                 315                 320

Asp Leu Thr Leu Asp Gly Asn Pro Phe Leu Asp Pro Gly Ala Leu Gln
                325                 330                 335

His Gln Asn Asp Pro Met Ile Ser Gly Val Val Pro Ala Cys Ala Arg
            340                 345                 350

Ser Ala Leu Thr Met Gly Val Ser Gly Ala Leu Ala Leu Leu Gln Gly
        355                 360                 365

Ala Arg Gly Phe Ala
    370

<210> SEQ ID NO 5
<211> LENGTH: 375
<212> TYPE: PRT
<213> ORGANISM: human

<400> SEQUENCE: 5

Met Glu Arg Ala Ser Cys Leu Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala

```
                35                  40                  45
Phe Gln Cys Val Ser Ala Val Glu Val Glu Ile His Ala Gly Gly Leu
     50                  55                  60

Asn Leu Glu Pro Phe Leu Lys Arg Val Asp Ala Asp Ala Asp Pro Arg
 65                  70                  75                  80

Gln Tyr Ala Asp Thr Val Lys Ala Leu Arg Val Arg Arg Leu Thr Val
                 85                  90                  95

Gly Ala Ala Gln Val Pro Ala Gln Leu Leu Val Gly Ala Leu Arg Val
                100                 105                 110

Leu Ala Tyr Ser Arg Leu Lys Glu Leu Thr Leu Glu Asp Leu Lys Ile
                115                 120                 125

Thr Gly Thr Met Pro Pro Leu Pro Leu Glu Ala Thr Gly Leu Ala Leu
                130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Tyr Glu Gln Val Arg Ala
                180                 185                 190

Phe Pro Ala Leu Thr Ser Leu Asp Leu Ser Asp Asn Pro Gly Leu Gly
                195                 200                 205

Glu Arg Gly Leu Met Ala Ala Leu Cys Pro His Lys Phe Pro Ala Ile
                210                 215                 220

Gln Asn Leu Ala Leu Arg Asn Thr Gly Met Glu Thr Pro Thr Gly Val
225                 230                 235                 240

Cys Ala Ala Leu Ala Ala Gly Val Gln Pro His Ser Leu Asp Leu
                245                 250                 255

Ser His Asn Ser Leu Arg Ala Thr Val Asn Pro Ser Ala Pro Arg Cys
                260                 265                 270

Met Trp Ser Ser Ala Leu Asn Ser Leu Asn Leu Ser Phe Ala Gly Leu
                275                 280                 285

Glu Gln Val Pro Lys Gly Leu Pro Ala Lys Leu Arg Val Leu Asp Leu
                290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
                340                 345                 350

Ala Arg Ser Thr Leu Ser Val Gly Val Ser Gly Thr Leu Val Leu Leu
                355                 360                 365

Gln Gly Ala Arg Gly Phe Ala
                370                 375

<210> SEQ ID NO 6
<211> LENGTH: 366
<212> TYPE: PRT
<213> ORGANISM: murine

<400> SEQUENCE: 6

Met Glu Arg Val Leu Gly Leu Leu Leu Leu Leu Val His Ala Ser
 1               5                  10                  15

Pro Ala Pro Pro Glu Pro Cys Glu Leu Asp Glu Glu Ser Cys Ser Cys
                20                  25                  30
```

```
Asn Phe Ser Asp Pro Lys Pro Asp Trp Ser Ser Ala Phe Asn Cys Leu
         35                  40                  45

Gly Ala Ala Asp Val Glu Leu Tyr Gly Gly Arg Ser Leu Glu Tyr
 50                  55                  60

Leu Leu Lys Arg Val Asp Thr Glu Ala Asp Leu Gly Gln Phe Thr Asp
 65                  70                  75                  80

Ile Ile Lys Ser Leu Ser Leu Lys Arg Leu Thr Val Arg Ala Ala Arg
                 85                  90                  95

Ile Pro Ser Arg Ile Leu Phe Gly Ala Leu Arg Val Leu Gly Ile Ser
             100                 105                 110

Gly Leu Gln Glu Leu Thr Leu Glu Asn Leu Val Thr Gly Thr Ala
         115                 120                 125

Pro Pro Pro Leu Leu Glu Ala Thr Gly Pro Asp Leu Asn Ile Leu Asn
     130                 135                 140

Leu Arg Asn Val Ser Trp Ala Thr Arg Asp Ala Trp Leu Ala Glu Leu
145                 150                 155                 160

Gln Gln Trp Leu Lys Pro Gly Leu Lys Val Leu Ser Ile Ala Gln Ala
                 165                 170                 175

His Ser Leu Asn Phe Ser Cys Glu Gln Val Arg Val Phe Pro Ala Leu
             180                 185                 190

Ser Thr Leu Asp Leu Ser Asp Asn Pro Glu Leu Gly Glu Arg Gly Leu
         195                 200                 205

Ile Ser Ala Leu Cys Pro Leu Lys Phe Pro Thr Leu Gln Val Leu Ala
     210                 215                 220

Leu Arg Asn Ala Gly Met Glu Thr Pro Ser Gly Val Cys Ser Ala Leu
225                 230                 235                 240

Ala Ala Ala Arg Val Gln Leu Gln Gly Leu Asp Leu Ser His Asn Ser
                 245                 250                 255

Leu Arg Asp Ala Ala Gly Ala Pro Ser Cys Asp Trp Pro Ser Gln Leu
             260                 265                 270

Asn Ser Leu Asn Leu Ser Phe Thr Gly Leu Lys Gln Val Pro Lys Gly
         275                 280                 285

Leu Pro Ala Lys Leu Ser Val Leu Asp Leu Ser Tyr Asn Arg Leu Asp
     290                 295                 300

Arg Asn Pro Ser Pro Asp Glu Leu Pro Gln Val Gly Asn Leu Ser Leu
305                 310                 315                 320

Lys Gly Asn Pro Phe Leu Asp Ser Glu Ser His Ser Glu Lys Phe Asn
                 325                 330                 335

Ser Gly Val Val Thr Ala Gly Ala Pro Ser Ser Gln Ala Val Ala Leu
             340                 345                 350

Ser Gly Thr Leu Ala Leu Leu Leu Gly Asp Arg Leu Phe Val
         355                 360                 365

<210> SEQ ID NO 7
<211> LENGTH: 377
<212> TYPE: PRT
<213> ORGANISM: rabbit
<220> FEATURE:
<221> NAME/KEY: unsure
<222> LOCATION: (14)
<223> OTHER INFORMATION: Xaa = unknown
<220> FEATURE:
<221> NAME/KEY: unsure
<222> LOCATION: (265)...(267)
<223> OTHER INFORMATION: Xaa = unknown
<220> FEATURE:
<221> NAME/KEY: unsure
<222> LOCATION: (269)
```

<223> OTHER INFORMATION: Xaa = unknown

<400> SEQUENCE: 7

```
Met Glu Pro Val Pro Cys Leu Leu Leu Leu Pro Xaa Leu Leu
  1               5                  10                  15

Arg Ala Ser Thr Asp Thr Pro Glu Pro Cys Glu Leu Asp Asp Asp
                 20                  25                  30

Ile Arg Cys Val Cys Asn Phe Ser Asp Pro Gln Pro Asp Trp Ser Ser
         35                  40                  45

Ala Leu Gln Cys Met Pro Ala Val Gln Val Glu Met Trp Gly Gly Gly
     50                  55                  60

His Ser Leu Glu Gln Phe Leu Arg Gln Ala Asp Leu Tyr Thr Asp Gln
 65                      70                  75                  80

Arg Arg Tyr Ala Asp Val Val Lys Ala Leu Arg Val Arg Leu Thr
                 85                  90                  95

Val Gly Ala Val Gln Val Pro Ala Pro Leu Leu Gly Val Leu Arg
             100                 105                 110

Val Leu Gly Tyr Ser Arg Leu Lys Glu Leu Ala Leu Glu Asp Ile Glu
         115                 120                 125

Val Thr Gly Thr Ala Pro Pro Pro Pro Leu Glu Ala Thr Gly Pro
         130                 135                 140

Ala Leu Ser Thr Leu Ser Leu Arg Asn Val Ser Trp Pro Lys Gly Gly
145                 150                 155                 160

Ala Trp Leu Ser Glu Leu Gln Gln Trp Leu Lys Pro Gly Leu Gln Val
                 165                 170                 175

Leu Asn Ile Ala Gln Ala His Thr Leu Ala Phe Ser Cys Glu Gln Val
             180                 185                 190

Arg Thr Phe Ser Ala Leu Thr Thr Leu Asp Leu Ser Glu Asn Pro Gly
         195                 200                 205

Leu Gly Glu Arg Gly Leu Val Ala Ala Leu Cys Pro His Lys Glu Pro
     210                 215                 220

Ala Leu Gln Asp Leu Ala Leu Arg Asn Ala Gly Met Lys Ile Leu Gln
225                 230                 235                 240

Gly Val Cys Ala Ala Leu Ala Glu Ala Gly Val Gln Pro His His Leu
                 245                 250                 255

Asp Leu Ser His Asn Ser Leu Arg Xaa Xaa Xaa Ala Xaa Asp Thr Gln
             260                 265                 270

Arg Cys Ile Trp Pro Ser Ala Leu Asn Ser Leu Asn Leu Ser Phe Thr
         275                 280                 285

Gly Leu Gln Gln Val Pro Lys Gly Leu Pro Ala Lys Leu Asn Val Leu
     290                 295                 300

Asp Leu Ser Cys Asn Lys Leu Asn Arg Ala Pro Gln Pro Gly Glu Leu
305                 310                 315                 320

Pro Lys Val Val Asn Leu Ser Leu Asp Gly Asn Pro Phe Leu Val Pro
                 325                 330                 335

Gly Ala Ser Lys Leu Gln Glu Asp Leu Thr Asn Ser Gly Val Phe Pro
             340                 345                 350

Ala Cys Pro Pro Ser Pro Leu Ala Met Gly Met Ser Gly Thr Leu Ala
         355                 360                 365

Leu Leu Gln Gly Ala Arg Gly Phe Ile
     370                 375
```

<210> SEQ ID NO 8
<211> LENGTH: 1405

<212> TYPE: DNA
<213> ORGANISM: bovine

<400> SEQUENCE: 8

```
gcgtgacgca ctgtaaagga aagaatccac agtccagccc gacaaccaga gagagaggca      60
caggctctga gaatctactg actatgttct tggggccgaa gcgtgggcta tttggggact     120
taggaacagg cttgggccgc cctgacctcc gctgtcgggc caggtgtgcg tgccctacct     180
gctgctgctg ctgctgccgt cactgctgcg tgtgtctgcg gacacaacag aaccctgcga     240
gctggacgac cacgatttcc gttgtgtctg caacttcacg gatccgaagc ctgactggtc     300
tagcgccgtt cagtgtatgg ttgccgtcga ggtggagatc agtgccggcg ccgcagcct      360
ggaacagttt ctcaagggag ccgacaccaa cccgaagcag tatgctgaca caatcaaggc     420
tctgcgcgtt cggcgactca agctgggcgc tgcacaggtt cctgctcagc ttctggtcgc     480
cgttctgcgc gcgctcgggt actctcgtct caaggaactg acgcttgagg acctggaggt     540
aaccggccca acgccccga cgcctctgga agccgctggg cctgcgctca ccaccctcag     600
tctgcgtaac gtatcgtgga caacaggagg tgcctggctc ggcgaactgc agcagtgcct     660
caagcctggg ctcagggtgc tgaacattgc ccaagcacac tcgcttgcct ttccgtgcgc     720
agggctctcc accttcgagg cgctcaccac cctagacctg tctgacaatc ccagtctcgg     780
cgacagcggg ctgatggcag ctctctgtcc gaacaagttc ccggccctcc aatatctagc     840
gctacgcaac gcggggatgg agacgccgag cggcgtgtgc gcggcgctgg cggcagcgag     900
ggtgcagccc caaagcctgg acctcagcca caactcgctg cgcgtcaccg ccccgggtgc     960
tacccgatgt gtctggccca gtgcactaag gtctctcaat ttgtcgttcg ctgggctgga    1020
gcaagtgcct aagggactgc cccctaagct cagcgtgctt gatctcagct gcaacaagct    1080
aagcagggag ccgcggcgag acgagctgcc cgaggtaaat gacctgactc tggacggaaa    1140
tcccttcctg gaccctggag ccctccagca ccaaaatgac ccgatgatct ccggcgtggt    1200
cccagcctgt gcgcgttctg ccttgaccat ggggtgtca ggagccctgg cgctgcttca    1260
aggagcccga ggcttcgcgt aaggccaggg aagagaggg aagaggaatg aattggctca    1320
gattgccctg gctccgggag accctcgcca ggacatctca accaaccagc ttctgccccc    1380
atccttatta aaatcttaaa cagca                                         1405
```

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Chemically synthesized polypeptide

<400> SEQUENCE: 9

Leu Leu Leu Leu Leu Leu Pro Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Chemically synthesized polypeptide

<400> SEQUENCE: 10

Leu Leu Leu Leu Leu Leu Pro Leu

-continued

```
<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 11

Leu Leu Leu Leu Leu Leu Val His
1               5
```

INDUCTION OF ANTIBIOTIC PROTEINS AND PEPTIDES BY LAIT/SCD14-PROTEIN

This application is a continuation of prior Ser. No. 09/721,904 filed Nov. 27, 2000, which application is a continuation of prior application Serial No. PCT/CA 99/00482 filed May 27, 1999, which application claims priority from U.S. Provisional Patent Application Ser. No. 60/086,884 filed May 27, 1998, all of which applications are incorporated herein by reference. International patent application No. PCT/CA 99/00482 was published in English under Article 21 of the Patent Cooperation Treaty under WO 99/61468 on Dec. 2, 1999 without the International Search Report, and again under WO 99/61468 on Apr. 6, 2000 with the International Search Report.

FIELD OF INVENTION

This invention relates to soluble LAIT-protein (CD14) derived from mammals, and related proteins, that directly induce the expression of antibiotic polypeptides, particularly, defensins in mammalian cells, particularly epithelial cells. This invention also relates to the identification of a portion of CD14 necessary for the direct activation of B cells by CD 14.

Peptide Antibiotics and their Induction by Endotoxin

Antibiotic peptides are widely distributed in nature, and comprise a widespread mechanism of host defense (Lehrer, R. I. et. al. 1993. *Ann. Rev. Immunol.* 11:105; Boman, H. G. 1995. *Ann. Rev. Immunol.* 13:61; Lehrer, R. I., T. Ganz, and M. E. Selsted. 1991. *Cell* 64:229; Zasloff, M. 1992. *Curr. Opin. Immunol.* 4:3). An advantage of peptide antibiotics as factors of the innate immune system is their ability to function without specificity, and without memory. Their anti-bacterial, anti-viral, and anti-fungal activities permit the host to delay or possibly even avoid microbial growth shortly after infection, before the adaptive immune response can be mobilized (Lehrer, R. I. et al. 1993. *Ann. Rev. Immunol.* 111:105; Boman, H. G. 1995. *Ann. Rev. Immunol.* 13:61; Lehrer, R. I., T. Ganz, and M. E. Selsted. 1991. *Cell* 64:229; Zasloff, M. 1992. *Curr. Opin. Immunol.* 4:3). Defensins are the largest family of antibiotic peptides, and are composed of 29 to 35 amino acid residues, and constitute greater than 5% of total cellular protein in human neutrophils (Boman, H. G. 1995. *Ann. Rev. Immunol.* 13:61; Lehrer, R. I., T. Ganz, and M. E. Selsted. 1991. *Cell* 64:229; Zasloff, M. 1992. *Curr. Opin. Immunol.* 4:3). In mammals defensins are also known to be produced by lung macrophages (Lehrer, R. I. et. al. 1993. *Ann. Rev. Immunol.* 11:105; Boman, H. G. 1995. Ann. Rev. Immunol. 13:61; Lehrer, R. I., T. Ganz, and M. E. Selsted. 1991. Cell 64:229; Zasloff, M. 1992. Curr. Opin. Immunol. 4:3), and have most recently been described in bovine epithelial cells of the trachea (Diamond, G. J. P. Russell, and C. L. Bevins. 1996. *PNAS* 93:5156) and tongue (Schonwetter, B. S., Stolzenberg, E. D. and M. A. Zasloff. 1995. *Science* 267:1645).

It has been demonstrated that endotoxin, in the form of lipopolysaccharide (LPS), induces a ten-fold increase in the expression of messenger RNA (mRNA) encoding an antibiotic peptide in primary tracheal epithelial cells (Diamond, G. J. P. Russell, and C. L. Bevins. 1996. *PNAS* 93:5156). This peptide, termed tracheal antibiotic peptide (TAP), is of the β-defensin class. The mechanism of TAP induction from epithelial cells of the respiratory mucosa was shown to be mediated through membrane CD14 (mCD14) expressed on the epithelial cells. The role of epithelial mCD14 was consistent with the observation that the activation process resulting in TAP expression was inhibited in the presence of monoclonal antibody (mAb) specific for CD14 (Diamond, G. J. P. Russell, and C. L. Bevins. 1996. PNAS93:5156).

While the expression of mCD14 was thought for some time to be an exclusive marker of monocytes macrophages (Zeigler-Heitbrock, H. W. L. and R. J. Ulevitch. 1993. *Immunology Today* 14:121), it is now known to be expressed by epithelial cells derived from many tissues (Fearns, C. et. al. 1995. J. Exp. Med. 181:857). It has also been found that epithelial linings of other tissues respond to endotoxin or inflammation through the local production of defensins. In particular, the squamous epithelial lining of the tongue has been shown to respond to infection or inflammation with the production of β-defensin lingual antibiotic peptide (Schonwetter, B. S., Stolzenberg, E. D. and M. A. Zasloff. 1995. *Science* 267: 1645). In this study, messenger RNA (mRNA) encoding lingual antimicrobial peptide was shown to be present in great abundance in epithelial cells of the tongue that surrounded naturally occurring lesions. There has apparently been no report of mCD14 involvement in this context.

The results described above provide the experimental basis for an immune response model in which innate immune response machinery is engaged at local sites of infection and/or inflammation so as to contribute to the initial defense of the host. The local production of antibiotic proteins and peptides in response to LPS derived from gram negative bacteria may thus come in to play in the prevention of bacterial colonization or subsequent infection prior to engagement of a clonal adaptive immune response. By way of background, a brief summary of the current understanding of mechanism(s) underlying endotoxin mediated responses in monocytes, macrophages, epithelial cells, and endothelial cells thus follows.

CD14 is a MEMBRANE Receptor on Monocytes for LPS: LBP Complexes.

Endotoxin in the form of LPS induces inflammatory cytokines by monocytes/macrophages both in vitro and in vivo (Beutler, B. et. al. 1986. *Science* 232:977; Michie, H. R. et. al. 1988. *New Engl. J. Med.* 318:1481; Tracey, K. J. et. al. 1987. *Nature* 330:662; Waage, A., Halstensen, A. and T. Espevik. 1987. *Lancet* 1:355). These monocyte-derived cytokines, including TNFβ, IL-1, and IL-6, are associated with septic shock syndrome, ultimately leading to multi-organ failure. Recent work has characterized CD14 as a monocyte receptor for LPS (Wright, S. D. et. al. 1990. Science 249:1431), which in turn led to the initial characterization of a mechanism through which LPS activates monocytes/macrophages.

The current paradigm posits the involvement of the constitutively expressed plasma protein, lipopolysaccharide-binding protein (LBP), which forms high affinity complexes with LPS (Schumann, R. R. et. al. 1990. *Science* 249:1429; Wright, S. D. et. al. 1990. *Science* 249:1431; Wright, S. D. et. al. 1989. *J. Exp. Med.* 170:1231). LBP is a plasma glycoprotein produced by the liver, present constitutively in plasma of healthy adult humans at 5-10 $\mu$g/ml, which has been shown to increase in concentration up to 20-fold after an acute phase response (Schumann, R. R. et. al. 1990. Science 249:1429; Tobias, P. S. et. al. 1992. Cell. Mol. Biol. 7:239; Tobias, P. S., Mathison, J. C. and R. J. Ulevitch 1988. *J. Biol. Chem.* 263: 13479; Tobias, P. S., Soldau, K. and R. J. Ulevitch 1986. *J. Exp. Med.* 164:777; Wright, S. D. et al 1990. *Science* 249: 1431; Wright, S. D. et. al. 1989. *J. Exp. Med.* 170:1231). Upon binding LBP, the ability of LPS to stimulate cytokine production in macrophages and monocytes is enhanced (Mathison, J. C., Tobias, P. S. and R. J. Ulevitch 1991. *Pathobiology* 59:185; Schumann, R. R. et. al. 1990. Science 249:

1429; Wright, S. D. et. al. 1990. *Science* 249:1431; Wright, S. D. et. al. 1989. *J. Exp. Med.* 170:1231).

Membrane CD14 (mCD14), tethered through a glycosylphosphatidylinositol anchor (Zeigler-Heitbrock, H. W. L. and R. J. Ulevitch. 1993. *Immunology Today* 14:121), functions as a receptor for LPS-LBP complexes (Schumann, R. R. et. al 1990. *Science* 249:1429; Wright, S. D. et. al. 1990. Science 249:1431). CD 14 is expressed at high levels on monocytes and macrophages, and weakly on neutrophils (Ball, E. D. et. al. 1982. *Proc. Natl. Acad. Sci. USA* 79:5374; Buckle, A. M., Jayaram, Y. and N. Hogg 1990. Clin. Exp. Immunol. 81:339; Ferrero, E. et. al. 1990. J. Immunol. 145: 331; Goyert, S. et. al. 1988. Science 239:497; Haziot, A. et. al. 1988. J. Immunol. 141:547). A murine pre-B cell line 70Z/3 (Paige, C. J. et. al. 1978. *J. Immunol.* 121:641), does not express detectable mCD14 by immunofluoresence, and is negative for message encoding CD14 as assessed by both northern blot analysis, and RT-PCR (Filipp, D. and M. Julius unpublished observation; Lee, J. D. et. al 1992. J. Exp. Med. 175:1697). This cell line has been used to provide compelling evidence for the role of mCD14 as a receptor for LPS-LBP complexes. Specifically, 70Z/3 responds to LPS with the expression of membrane immunoglobulin (mIg) (Paige, C. J. et. al. 1978. *J. Immunol.* 121:641). The concentration of LPS required to induce mIg expression in mCD14⁻ 70Z/3 is orders of magnitude higher than that required to stimulate cytokine production by mCD14⁺ monocytes (Lee, J. D. et. al. 1992. *J. Exp. Med.* 175:1697). When 70Z/3 is transfected with cDNA encoding human CD14, it was demonstrated that the concentration of LPS required to induce mIg expression by mCD14⁺ clones was 10,000-fold lower than that required in the wild-type mCD14⁻ parental line of 70Z/3 (Lee, J. D. et al. 1992. *J. Exp. Med.* 175:1697).

These results provide experimental evidence for the current model for in vivo LPS mediated activation of mCD14⁺ leukocytes. Upon exposure to LPS, LPS-LBP complexes form, and these complexes activate monocytes/macrophages through interaction with mCD14.

Soluble CD14 in Endotoxin Mediated Activation of Endothelial and Epithelial Cells.

In contrast to the suggested mechanisms involved in LPS mediated activation of mCD14⁺ leukocytes, less is understood about the mechanisms involved in LPS mediated activation of endothelial and epithelial cells. Until recently, endothelial and epithelial cells were thought to be mCD14⁺. Despite the undetectable expression of mCD14 in these cell types, LPS mediated activation has been shown to be serum dependent, and inhibited by monoclonal antibodies specific for CD14 (Patrick, D. et. al. 1992. *J. Inf Dis.* 165:865; Pugin, J. et. al. 1993. *Proc. Natl. Acad. Sci. USA* 90:2744; Arditi, M. et. al. 1993. *Infect. Immun.* 61:3149). This suggests that CD14 may play some role, albeit unknown, in endotoxin mediated activation of endothelial and epithelial cells.

It has been demonstrated that soluble CD14 (sCD14), lacking the glycosylphosphatidylinositol anchor, and present in serum of healthy adult humans (Bazil, V. et. al. 1986. *Eur. J. Immunol.* 16:1583), is involved in LPS mediated activation of both endothelial cells (Arditi, M. et. al. 1993. *Infect. Immun.* 61:3149; Pugin, J. et. al. 1993. *Proc. Natl. Acad. Sci. USA* 90:2744; Frey, E. A., et. al. 1992. *J. Exp. Med.* 176:1665; Read, M. A. et. al. 1993. *Proc. Natl. Acad. Sci. USA* 90:9887; Haziot, A. et. al. 1993. *J. Immunol.* 151:1500) and epithelial cells (Pugin, J. et. al. 1993. *Proc. Natl. Acad. Sci. USA* 90:2744). The serum dependence of the activation process was shown to be due to the presence of sCD14, and the requirement for serum could be replaced by sCD14. No role for LBP could be characterized in the case of LPS mediated endothelial cell activation in some studies, suggesting that sCD14 itself is an agonist for endothelial cell responses to endotoxin (Arditi, M. et. al. 1993. *Infect. Immun.* 61:3149; Frey, E. A., et. al. 1992. *J. Exp. Med.* 176:1665; Read, M. A. et. al. 1993. *Proc. Natl. Acad. Sci. USA* 90:9887). In other studies, a dual role for the serum in the LPS response for both endothelial and epithelial cells was found. Specifically, both sCD14 and LBP appeared to be required for endotoxin mediated endothelial cell activation (Pugin, J. et. al. 1993. *Proc. Natl. Acad. Sci. USA* 90:2744; Haziot, A. et. al. 1993. *J. Immunol.* 151:1500), most pronouncedly when endotoxin was present at low concentrations (Haziot, A. et. al. 1993. *J. Immunol.* 151:1500).

The above experimental results led to the postulated role of sCD14-LPS complexes in the activation of mCD14⁻ endothelial cells. At high LPS concentrations these complexes are thought to be generated directly through the interaction of sCD14 and LPS. At low LPS concentrations LBP is thought to first interact with LPS, which in as yet uncharacterized ways is postulated to facilitate the generation of sCD14-LPS complexes.

While the above results are potentially at odds with each other in regard to the suggested mechanisms supporting endothelial/epithelial cell responses to LPS, they share a common element in that the mechanism(s) are distinct from those involving endotoxin mediated activation of mCD14⁺ cells. Both studies suggest a role for sCD14 functioning as an agonist, enabling responses to endotoxin by mCD14⁻ cells rather than functioning as a receptor for LPS-LBP complexes on mCD14⁺ cells. However, more recent studies have demonstrated that this may not be the case, at least for epithelial cells.

Membrane CD14 in Endotoxin Mediated Induction of Defensins by Epithelial Cells.

As discussed above, a recent study demonstrated that endotoxin induces the expression of defensins in primary bovine tracheal epithelial cells (Diamond, G. J. P. Russell, and C. L. Bevins. 1996. *PNAS* 93:5156) and that the expression involved mCD14. While unstimulated epithelial cells were shown to be mCD14⁻, they were induced to a mCD14⁺ state subsequent to LPS mediated activation (Diamond, G. J. P. Russell, and C. L. Bevins. 1996. *PNAS* 93:5156). The induction of mCD14 on the primary tracheal epithelial cells was shown to correlate with the induction of message specific for CD14 in the epithelial cells, suggesting it was likely of endogenous origin. Further, LPS mediated induction of defensins was inhibited by mAb specific for CD14 (Diamond, G. J. P. Russell, and C. L. Bevins. 1996. *PNAS* 93:5156).

The mechanism(s) underlying LPS mediated activation of epithelial cells was thus shown to parallel those observed in mCD14⁺ monocytes and macrophages. The LPS activation pathways in these two cell types appear to differ from each other only in the basal levels of mCD14 expressed by the two types of target cells. Comparable studies involving endothelial cells have not been reported.

Soluble CD14 Directly Activates Monocytes in the Absence of Serum/LBP.

The paradigm described thus far is that endotoxin, in the form of LPS, mediates the activation of monocytes/macrophages and epithelial cells through its interaction with mCD14 on the cell. The serum dependence of this process, reflecting the involvement of LBP, has been demonstrated in all but one circumstance.

As described above, sCD14 has been implicated in endotoxin mediated activation/injury of endothelial cells. Its function was postulated as potentiating the interaction of LPS with the cell (Pugin, J. et al. 1993. *Proc. Natl. Acad. Sci USA* 90:2744). A subsequent study demonstrated that sCD14 isolated from the urine of nephrotic human subjects was able to directly stimulate the production of inflammatory cytokines, TNFβ and IL-6, by human monocytes (Sundan, A. et. al. 1994. *Eur. J. Immunol.* 24:1779). Human monocytes are mCD14$^+$, and LPS mediated induction of these two cytokines is serum dependent (Espevik, T. et. al. 1993. *Eur. J. Immunol.* 23:255; Wright, S. D. et. al. 1992. *J. Exp. Med.* 176:719). In contrast, the activity of sCD14 isolated from urine in this regard was shown to be serum independent, and was not affected by LBP, or by antibodies specific for LBP (Sundan, A. et. al. 1994. *Eur. J. Immunol.* 24:1779). Further, the capacity of sCD14 to stimulate the production of inflammatory cytokines by human monocytes was shown to be inhibited with mAb specific for CD14 (Sundan, A. et. al. 1994. *Eur. J. Immunol.* 24:1779).

Thus, sCD14 appears to have the capacity to directly interact with as yet unidentified receptor structures on monocytes in a serum independent fashion, and result in cytokine production. Endotoxin and sCD14 are thus able to mediate the similar biological responses in monocytes. Further, the ability of the same CD14 specific mAb, 3C10 (Van Voorhis, W. C. et. al. 1983. *J. Exp. Med.* 158:126), to inhibit both of these modes of stimulation, suggests that at least in part, signaling pathways involving endotoxin and sCD14 are shared, perhaps at the level of receptor structures. CD14 specific mAb 3C10 recognizes the N-terminal portion of CD14, and this recognition is dependent on the presence of the N-terminal amino acids 7 to 14 of the CD14 molecule (Juan, T. S.-C. et. al. 1995. *J. Biol. Chem.* 270:17237). The capacity of 3C10 to inhibit LPS mediated monocyte activation has been interpreted as reflecting the role of mCD14 residues 7 to 14 as an interaction site between mCD14 and LPS (Todd, S. C. et. al. 1995. *J. Biol. Chem.* 270:17237). In contrast, the basis for the capacity of mAb 3C10 to inhibit the function of sCD14 on monocytes in the absence of LPS is not clear (Sundan, A. et. al. 1994. *Eur. J. Immunol.* 24:1779). The simplest explanation suggests the presence of as yet uncharacterized receptor structures for sCD14 on monocytes, the mAb interfering with the interaction between sCD14 and such structure(s).

Soluble CD14 Inhibits the LPS-Induced Activation of Monocytes and Neutrophils in Vitro in a Dose Dependent Fashion International patent application published under No. WO 93/19772 on Oct. 14, 1993 describes inhibition of LPS-induced activation of monocytes and neutrophils in vitro by recombinant human soluble CD14 in a dose-dependent fashion, at least as indicated by data shown in FIG. 1 of the published document. The experiments were carried out in the presence of LPS-LBP complex and are consistent with binding of the complex and the added CD14 present so as reduce the degree of interaction between the complex and membrane-bound CD14 of the monocytes and neutrophils. Such a result is curious in that it is known that sCD14 is itself capable of stimulating production of inflammatory cytokines by monocytes.

Lactation-Associated ImmunoTrophic (LAIT)-Protein and B Cell Activation.

The description of the isolation, characterization of biological activities, molecular cloning and expression of recombinant LAIT-protein (bovine CD14) is described in co-pending U.S. patent application Ser. No. 08/746,883 filed Nov. 18, 1996 and the International Patent Application Serial No. PCT/CA97/00880 filed Nov. 18, 1997. Relevant portions of these prior applications are reproduced herein.

A protein was isolated from bovine and human colostrum and breast milk, which protein has been termed Lactation-Associated Immuno-Trophic (LAIT)-protein.

The biological activities of LAIT-protein distinguish it from all other known cytokines that support B-cell growth and differentiation in adult animals, and thus may play a unique role in the regulation of B cell activation. The induction of most humoral immune responses in the adult involves a sequence of cellular interactions among "helper" T lymphocytes, antigen presenting cells (APC), and B lymphocytes (Sprent, J. J. 1978. *J. Exp. Med.* 147:1159; Andersson, J. et. al. 1982. *Proc. Natl. Acad. Sci. USA* 77:1612; Julius, M. H. et. al. 1982. *Proc. Natl. Acad. Sci. USA* 79:1989). These interactions are mandatory (Sprent, J. J. 1978. *J. Exp. Med.* 147: 1159; Andersson, J. et. al. 1982. *Proc. Natl. Acad. Sci. USA* 77:1612; Julius, M. H. et. al. 1982. *Proc. Natl. Acad. Sci. USA* 79:1989; Julius, M. H. et. al. 1987. *Immunol. Rev.* 95:914), and thus reflect the role of specific plasma membrane associated molecules as transducers of prerequisite activation signals. The essential molecular interaction, reflected by the requirement for T cell-B cell contact, is mediated by CD40 expressed on the plasma membrane of the B cell, and its cognate ligand, gp39 (or CD40L), expressed on the plasma membrane of the T cell (Noelle, R. J. et. al. 1992. *Proc. Natl. Acad. Sci. USA* 89:6550; Armitage, R. J. et. al. 1992. *Nature* 357:80). The interaction between CD40 and CD40L predicates the induction of B cell growth, B cell differentiation into immunoglobulin secreting cells, and immunoglobulin isotype switching (Foy, T. M. et. al. 1993. *J. Exp. Med.* 178: 1567). Moreover, the array of cytokines produced by these interacting cells are central to the regulation of B lymphocyte activation, growth, and differentiation (Andersson, J. et. al. 1982. *Proc. Natl. Acad. Sci. USA* 77:1612; Noelle, R. J. et. al. 1983. *Proc. Natl. Acad. Sci. USA* 80:6628; Hodgkin, P. D. 1990. *J. Immunol.* 145:2025; Noelle, R. J. et. al. 1991. *J. Immunol.* 146:1118; Parker, D. C. 1980. *Immunol. Rev.* 52:115; Howard, M. et. al. 1982. *J. Exp. Med.* 155:914). These soluble mediators of lymphocyte activation do not act in isolation. Rather, they supplement one another, each driving the B lymphocyte to the next stage of activation, rendering them susceptible to subsequent and progressive activation signals (Julius, M. H. et. al. 1987. *Immunol. Rev.* 95:914).

LAIT-protein, in contrast, is directly mitogenic for B cells at nM concentrations, and functions as a co-stimualtor of B cell growth in combination with stimulation through the B cell antigen receptor in the pM range. In these latter circumstances, those signals derived from antigen convert the B cell into a physiological state in which it can receive T cell help. The pertinence of supplying the neonate with a factor that directly supports B cell growth and differentiation in combination with antigen is significant when one considers the suppressed state of T cells in a developing neonate.

It has been demonstrated that while the thymus efficiently produces T cells early in ontogeny, unlike the adult thymus (Bill, J. et. al. 1989. *J. Exp. Med.* 169:1405; MacDonald, H. R. et. al. 1988. *Nature* 332:4020), it does not efficiently delete those T cells expressing potentially autoreactive antigen receptors (Schneider, R. et. al. 1989. *J. Exp. Med.* 169:2149; Smith, H. et. al. 1989. *Science* 245: 749; Ceredig, R. 1990. *Intl. Immunol.* 2:859; Ceredig, R. and C. Waltzinger. 1990. Intl. Immunol. 2:869). At the same time, these neonates are healthy. Colostrum and early breast milk contain well characterized inhibitors of T cell function, particularly, TGFβ1 and TGFβ2, which are inhibitors of T cell activation (Spom, M. B. et. al. 1987. *J. Cell. Biol.* 105:1039; Massagué, J. 1987. *Cell* 49:437; Wrann, M. et. al. 1987. *EMBO J.* 6:1633; Stoeck, M. et. al. 1989. J. Immunol. 143:3258). It is therefore plausible that T cell function in neonates is actively suppressed by these cytokines to allow time for the maturation of thymic function. It is also of obvious importance for the neonate to initiate the production of its own protective antibodies, given that maternally-derived and passively acquired Ig is both transient and contains specificities that reflect maternal antigen encounter. It is expected that LAIT-protein functions as a T cell surrogate, supporting the growth and differentiation of B cells in the neonate freshly exposed to environmental antigens. The operation of LAIT-protein thus offers an alternative, truncated route for activating the immune system, which is independent of T cell function.

Sequencing analysis of bovine LAIT-protein fragments revealed high homology with human CD14. CD14 was subsequently purified from human colostrum by affinity chromatography using available monoclonal antibodies, and was shown to possess the same range of biological activities as colostral bovine LAIT-protein. The gene encoding bovine LAIT-protein was cloned from a bovine cDNA library, and shown to be highly homologous to human CD14, at both nucleotide and protein levels.

Recombinant human and mouse CD14, as well as recombinant bovine LAIT-protein/CD14 was prepared in both insect cell and mammalian cell expression systems, and each were shown to contain all of the biological activities of native bovine LAIT-protein of colostral origin, with specific activities within a factor of two of that observed with native material isolated from each of the three species.

In the context of this invention, "antibiotic proteins" or "antibiotic polypeptides" are with antibiotic properties: (i) linear, mostly helical peptides without cysteine, with or without a hinge (cecropins); (ii) linear peptides without cysteine and with a high proportion of certain residues such as proline and arginine; (iii) antibacterial peptides with one disulfide bond; (iv) peptides with two-or more S—S bonds giving mainly or only β-sheet structures including but not limited to human defensin, HNP-1, rabbit defensin NP-1, rat defensin NP-1, bovine β-defensin, TAP, pig protegrin, PG-3, and H-s crab tachypiesin 1; and (v) antibacterial peptides derived from larger polypeptides with other known functions (Boman, H. G. 1995. Ann. Rev. Immunol. 13:61).

"Defensins" are a subgroup of antibiotic polypeptides (Edwards, S. W. Biochemistry and Physiology of the Neutrophil, 1994. Cambridge University Press pp 67-70).

"Sepsis" is condition which manifests itself in a human patient, when invaded by a microbial agent, a temperature of greater than 38° C. or less than 36° C.; a heart rate of greater than 90 beats per minute; a respiratory rate of greater than 20 breaths per minute or $PaCO_2$ less than 32 mm Hg; a white blood cell count of greater than 12,000 $mm^{-3}$, less than 4,000 $mm^{-3}$ or greater than 10% immature (band) forms; organ dysfunction, hypoperfusion, or hypotension. Hypoperfusion and perfusion abnormalities may include, but are not limited to lactic acidosis, oliguria, or an acute alteration of mental states (1992. Chest 101:1644).

In the context of this application, CD14, unless otherwise indicated means any of bovine, human and murine CD14 proteins, recombinant or isolated from a naturally occurring source ("native"), the sequences of which correspond to SEQ ID NO:4; SEQ ID NO:5 and SEQ ID NO:6, respectively.

The present invention provides a method of ameliorating the symptoms of sepsis. According to this first aspect of the invention, there is a step of directly exposing epithelial cells of a mammal in need thereof to an effective amount of a compound comprising (i.e., which is made up of or includes) soluble CD14, or a polypeptide fragment of the CD14 that stimulates expression of a defensin in epithelial cells, or a conservatively substituted variant of said CD14 or the fragment that stimulates said expression.

The invention also includes a method of enhancing expression of defensins in a mammal in need thereof, by administering a compound comprising soluble CD14 or a polypeptide portion of CD14 that enhances said expression, or a conservatively substituted variant of said CD14 or the portion that enhances said expression.

The administering step includes preferably includes directly exposing epithelial cells of the mammal to said compound.

The invention includes a method of stimulating expression of one or more defensins by epithelial cells by administering thereto an effective amount of a compound comprising soluble CD14 or a polypeptide fragment of CD 14 that stimulates said expression, or a conservatively substituted variant of said CD14 or the fragment that enhances said expression.

The invention includes stimulating expression of a defensin along the gastrointestinal tract, or along the respiratory tract, of a mammal comprising exposing the tract to an effective amount of a compound comprising soluble CD14 or a polypeptide fragment of CD14 that stimulates said expression, or a conservatively substituted variant of said CD14 or the fragment that stimulates said expression.

Expression of a defensin takes place on the tongue of a mammal according to a certain aspect. Expression of a defensin can be in the intestine, particularly, the small intestine of a mammal.

According to a general aspect of the invention, expression of defensins by epithelial cells of a mammal is induced.

The CD14 can have an amino acid sequence selected from the group consisting of SEQ ID NO:4, SEQ ID NO:5, SEQ ID NO:6 or SEQ ID NO:7, or a conservatively substituted variant thereof.

In another aspect, the invention is a method of ameliorating the symptoms of sepsis comprising administering to a mammal in need thereof an effective amount of a soluble protein so as to directly expose epithelial cells of the mammal to the protein, the protein having an amino acid sequence which is at least about 63% conserved in relation to the amino acid sequence identified as SEQ ID NO:5 and having the ability to induce expression of defensins in epithelial cells.

Alternatively, the protein can have an amino acid sequence which is at least about 68% or about 71% or about 73% or about 78% or about 83% or about 88% or about 93% or about 98% conserved in relation to the amino acid sequence identified as SEQ ID NO:5.

The invention includes a method for prophylactically treating a lipopolysaccharide-induced host inflammatory response in a mammal, which method comprises administering a therapeutically effective amount of an effective amount of a protein to the mammal so as to directly expose epithelial cells of the mammal to the protein, the protein having an amino acid sequence which is at least about 63% conserved in relation to the amino acid sequence identified as SEQ ID NO:4 or identified as SEQ ID NO:5 or identified as SEQ ID NO:6 and having the ability to enhance expression of one or more defensins in bovine epithelial cells.

The invention includes a method of enhancing expression of defensins in a mammal in need thereof, by administering an effective amount of a soluble protein to the mammal, the protein having an amino acid sequence which is at least about 63% conserved in relation to the amino acid sequence identified as SEQ ID NO:4 or identified as SEQ ID NO:5 or identified as SEQ ID NO:6 and having the ability enhance expression of defensins in mammalian epithelial cells.

The invention includes a method of stimulating expression of one or more defensins by epithelial cells by exposing the cells to an effective amount of a soluble protein, the protein having an amino acid sequence which is at least about 63% conserved in relation to the amino acid sequence identified as SEQ ID NO:4 or identified as SEQ ID NO:5 or identified as SEQ ID NO:6 and having the ability to stimulate expression of one or more defensins in epithelial cells.

The invention includes a method of stimulating expression of a defensin along the gastrointestinal tract of a mammal comprising exposing the tract to an effective amount of a soluble protein, the protein having an amino acid sequence which is at least about 63% conserved in relation to the amino acid sequence identified as SEQ ID NO:4 or identified as SEQ ID NO:5 or identified as SEQ ID NO:6 and having the ability to stimulate expression of a defensin in bovine epithelial cells.

The invention includes a method of stimulating expression of a defensin along respiratory tract and/or on the tongue, or in the small intestine, of a mammal comprising exposing the tongue to an effective amount of a soluble protein, the protein having an amino acid sequence which is at least about 63% conserved in relation to the amino acid sequence identified as SEQ ID NO:4 or identified as SEQ ID NO:5 or identified as SEQ ID NO:6 and having the ability to stimulate expression of a defensin in epithelial cells.

The invention includes a method of inducing expression of defensins by epithelial cells of a mammal in need thereof, the method comprising administering and effective amount of a protein, the protein having an amino acid sequence which is at least about 63% conserved in relation to the amino acid sequence identified as SEQ ID NO:4 or identified as SEQ ID NO:5 or identified as SEQ ID NO:6 and having the ability to induce expression of defensins in epithelial cells.

The CD14 or the polypeptide portion or the variant can be obtained recombinant or chemical methods.

In another aspect, the invention is a method of preparing a CD14 concentrate. The method includes providing a stock solution containing protein of a mammary secretion, separating from the solution a concentrate comprising endogenous CD14; and determining the concentration of CD14 in the concentrate.

The mammary secretion can be milk, whole milk or a protein-containing portion of whole milk, or it can be colostrum or a protein-containing portion of colostrum.

Preferably, the secretion has been previously subjected to a treatment step, and the treatment step is sufficiently mild to permit preservation of the CD14 activity for inducing or stimulating defensin production and/or for stimulating B cells.

The mammary secretion can be human or it can be bovine. In situations in which the CD14 is obtained from a mammal in which it occurs endogenously (i.e., in a mammal which has not been the subject of molecular genetic manipulations), the CD14 is preferably bovine.

In cases where the solution is a liquid solution the separating step can include salting out of proteins from the solution.

Determining the concentration of CD14 can include exposing a sample obtained from the concentrate to a first antibody specific for CD14 to form an antibody-CD14 complex and subsequently exposing the complex to a second antibody specific for CD14, wherein the second antibody includes a reporter molecule. ELISA assays are particularly convenient in this regard.

Determining the concentration of CD14 can include exposing a sample obtained from the concentrate to a first antibody specific for CD14 to form an antibody-CD14 complex and subsequently exposing the complex to a second antibody specific for the first antibody, wherein the second antibody includes a reporter molecule.

In another aspect, the invention is a method of obtaining CD14 which includes providing a stock solution containing protein of a mammary secretion, precipitating from the stock solution a protein fraction containing CD14 and isolating the protein fraction from the supernatant.

Precipitation can include salting out a protein fraction containing CD14. Preferably, the salt concentration of the solution is increased to obtain an ionic strength at least as high as would be obtained by combining a saturated aqueous solution of ammonium sulphate with a volume of a said mammary secretion (as it occurs naturally), in which the volume of the ammonium sulphate solution being equal to 65 percent of the total volume of the combined solutions.

The method often includes also determining the amount of CD14 obtained in the isolating step.

Again, the mammary secretion can be colostrum and/or milk and can be bovine or human, or from another type of mammal in which CD14 occurs in mammary secretions.

The invention includes another method of obtaining CD14, that involves providing a stock solution comprising protein of a mammary secretion; and isolating from the solution a fraction containing proteins that are insoluble in the mammary secretion upon combining a saturated aqueous solution of ammonium sulphate with a volume of a said mammary secretion, the volume of the ammonium sulphate solution being equal to 65 percent of the total volume of the combined solutions. Preferably, the method includes a step of determining the amount of CD14 obtained in the isolating step.

Endogenous CD14 proteins obtained according to methods of the invention can be used for directly activating B cells when in a suitably soluble form. Likewise, they can be used in producing medicaments for such use.

According to another aspect, the invention is a method for testing for the presence of CD14 in a composition containing protein of a mammary secretion. The method includes exposing the composition to an antibody which is specific for CD14; and determining whether CD14 endogenous to the secretion is present in the sample based on whether CD14-antibody complex has formed in the exposing step.

The secretion may or may not have been previously subjected to a treatment step, but if it has the treatment step is sufficiently mild to permit preservation of the CD14 activity for inducing or stimulating defensin production and/or for stimulating B cells.

Again, preferably, the method includes determining the concentration of CD14 in the sample.

In another aspect, the invention is a method of preventing, ameliorating or treating the symptoms of sepsis in a mammal, comprising administering to the mammal an effective amount of CD14 obtained from a mammalian mammary secretion.

Preferably, the CD14 is obtained from a mammary secretion according to one of the methods therefor described herein.

The CD14 can be contained in a liquid and the liquid can include a fraction of the milk enriched in CD14. The CD14 can be contained in an edible product, such as a food bar (e.g., chocolate or protein bar).

In another aspect, the invention includes a method for determining the amount of endogenous CD14 contained in a composition containing protein of a mammary secretion, i.e., on an animal not subject to molecular genetic manipulation as far as CD14 production is concerned. The method includes providing the composition; exposing a sample of the composition to an antibody which is specific for CD14 and determining the amount CD14 endogenous to the secretion present in the sample based on the amount of CD14-antibody complex formed in the exposing step.

The invention includes a method for determining the suitability of a product derived from a mammary secretion for use in inducing or stimulating defensin production in mammals, the method comprising the steps of:

providing a sample of the product; and determining the amount of CD14 present in the sample.

This aspect of the invention could thus be used as a preliminary step in determining the amount of such product is to be incorporated into a medicament or food product etc., to be used according to a method of this invention, or other method for which soluble CD14 is known to be useful.

Accordingly, it is preferable that, if the secretion has been previously subjected to a treatment step, the treatment step is sufficiently mild to permit preservation of the CD14 activity for inducing or stimulating said defensin production.

Likewise, the invention includes a method for determining the suitability of a product derived from a mammary secretion for use in stimulating B cells in mammals, the method comprising the steps of: providing a sample of the product; and determining the amount of endogenous CD14 present in the sample.

In preferred aspects, an antibody is used in the determining step and more preferably, the antibody is mAb 3C10 and/or a mAb that recognizes the same amino acid sequence as mAb 3C10.

The invention includes the use of compounds described herein for the preparation of a medicament for use in ameliorating the symptoms of sepsis, for use in enhancing expression of defensins in a mammal, etc.

Another aspect of the invention includes a method of enhancing expression of defensins in a mammal in need thereof, comprising administering to a mammal in need thereof an effective amount of a recombinant polypeptide CD14 encoded by a non-naturally occurring recombinant DNA molecule comprising a first DNA sequence selected from the group consisting of:

(a) a cDNA sequence encoding CD14 according to SEQ ID NO:2;

(b) a DNA sequence which specifically hybridizes to the noncoding strand of (a) and which codes on expression for a polypeptide specifically recognized by an antibody which also specifically recognizes human CD14; and (c) a DNA sequence which encodes the same polypeptide as is encoded by a DNA sequence of (a) or (b) above; wherein the polypeptide encoded by (b) or (c) enhances said expression.

Yet another aspect of the invention is a method of stimulating expression of one or more defensins by epithelial cells comprising administering to a mammal in need thereof an effective amount of a recombinant polypeptide CD14 encoded by a non-naturally occurring recombinant DNA molecule comprising a first DNA sequence selected from the group consisting of:

(a) a cDNA sequence encoding CD14 according to SEQ ID NO:2;

(b) a DNA sequence which specifically hybridizes to the noncoding strand of (a) and which codes on expression for a polypeptide specifically recognized by an antibody which also specifically recognizes human CD14; and (c) a DNA sequence which encodes the same polypeptide as is encoded by a DNA sequence of (a) or (b) above;

wherein the polypeptide encoded by (b) or (c) stimulates said expression.

Preferably, the specific hybridization is under stringent hybridization conditions.

"Stringent hybridization conditions" takes on its common meaning to a person skilled in the art here. Appropriate stringency conditions which promote nucleic acid hybridization, for example, 6× sodium chloride/sodium citrate (SSC) at about 45° C. are known to those skilled in the art. The following examples are found in Current Protocols in Molecular Biology, John Wiley & Sons, NY (1989), 6.3.1-6.3.6: For 50 ml of a first suitable hybridization solution, mix together 24 ml formamide, 12 ml 20×SSC, 0.5 ml 2 M Tris-HCl pH 7.6, 0.5 ml 100× Denhardt's solution, 2.5 ml deionized $H_2O$, 10 ml 50% dextran sulfate, and 0.5 ml 10% SDS. A second suitable hybridization solution can be 1% crystalline BSA (fraction V), 1 mM EDTA, 0.5 M $Na_2HPO_4$ pH 7.2, 7% SDS. The salt concentration in the wash step can be selected from a low stringency of about 2×SSC at 50° C. to a high stringency of about 0.2×SSC at 50° C. Both of these wash solutions may contain 0.1% SDS. In addition, the temperature in the wash step can be increased from low stringency conditions at room temperature, about 22° C., to high stringency conditions, at about 65° C. The cited reference gives more detail, but appropriate wash stringency depends on degree of homology and length of probe. If homology is 100%, a high temperature (65° C. to 75° C.) may be used. If homology is low, lower wash temperatures must be used. However, if the probe is very short (<100 bp), lower temperatures must be used even with 100% homology. In general, one starts washing at low temperatures (37° C. to 40° C.), and raises the temperature by 3-5° C. intervals until background is low enough not to be a major factor in autoradiography.

Preferably, such a polypeptide is specifically recognized by an antibody which also specifically recognizes human CD14, such as mAb 3C10.

Methods of the invention can include direct topical exposure of the epithelium of the trachea, or of the outer epidermis of a mammal, particularly of wounds, to the polypeptide or protein, as the case may be.

The invention thus also includes a method of preparing an ointment for direct topical application to a wound of human skin for ameliorating the effects of infection, particularly bacterial infection, thereof, comprising incorporating into the ointment an effective amount of a concentrate or other compound of the invention having CD14 defensin inducing activity.

Likewise, an infant formula, milk or other liquid having added thereto a fraction of a milk product, the fraction including a higher concentration of CD14 than occurs naturally in the unfractionated milk product, wherein the milk product is one which has not been treated by a process which denatures the CD14 contained therein to the extent that CD14 loses the desired activity, is part of the invention.

Compositions and methods of the invention can be used for a mammal that is in need of protection against a microbial pathogen selected from the group consisting of virus, bacteria, fungus and yeast, particularly where the mammal a human suffering from immune deficiency.

Induced defensins include RtNP1, RtNP2, RtNP3, RtNP4, HNP1, HNP2, and HNP3 and any combination thereof, or of HNP1, HNP2, and HNP3, and any combination thereof.

Preferably, the protein or polypeptide of the invention, as the case may be, is administered in an amount of between about 250 μg to about 2500 μg per kg of bodyweight of the mammal per day or in an amount of between about 300 μg to about 1 mg per kg of bodyweight per day.

In another aspect, the invention is a method of directly activating B cells using a soluble polypeptide having the amino acid sequence selected from the group consisting of leu-leu-leu-leu-leu-leu-pro-ser (SEQ ID NO:9); leu-leu-leu-leu-leu-leu-pro-leu (SEQ ID NO:10); and leu-leu-leu-leu-leu-leu-val-his (SEQ ID NO:11), and which is specifically recognized by the monoclonal antibody 3C10 and which activates B cells.

Preferably in such a method, the amino acid comprises a sequence selected from the group consisting of SEQ ID NO:4, SEQ ID NO:5 or SEQ ID NO:6 or a conservatively substituted variant thereof which activates B cells, or a fragment thereof which activates B cells or a conservatively substituted variant thereof which activates B cells.

The invention includes a transgenic mammal having introduced into its genome a nucleic acid sequence encoding a polypeptide having the amino acid sequence identified as SEQ ID NO:4, SEQ ID NO:5, or SEQ ID NO:6, or fragment of said polypeptide which directly activates B cells; or a variant of said polypeptide which directly activates B cells; a conservatively substituted variant of the polypeptide; or conjugates of the fragment or variant thereof which directly activates B cells, wherein the nucleic acid sequence is under control of a CD14 promoter endogenous to the mammal and the nucleic acid sequence is in addition to nucleic acid sequences which naturally occur in the DNA of the mammal.

The nucleic acid sequence optionally encodes a polypeptide having the amino acid sequence identified as SEQ ID NO:4, SEQ ID NO:5, or SEQ ID NO:6, or fragment of said polypeptide which directly activates B cells; or a conservatively substituted variant of the polypeptide, more preferably, a polypeptide having the amino acid sequence identified as SEQ ID NO:4, SEQ ID NO:5, or SEQ ID NO:6, or a conservatively substituted variant of the polypeptide and even more preferably, a polypeptide having the amino acid sequence identified as SEQ ID NO:4, SEQ ID NO:5, or SEQ ID NO:6. Most preferably, the nucleic acid sequence has the sequence identified as SEQ ID NO:1 or SEQ ID NO:2.

Preferably, the transgenic mammal has introduced into its genome a nucleic acid sequence encoding a protein capable of directly activating B cells using a soluble polypeptide having the amino acid sequence selected from the group consisting of leu-leu-leu-leu-leu-leu-pro-ser; leu-leu-leu-leu-leu-leu-pro-leu; and leu-leu-leu-leu-leu-leu-val-his, and which is specifically recognized by the monoclonal antibody 3C10 and which activates B cells.

A transgenic mammal can alternatively have introduced into its genome a nucleic acid sequence encoding other proteins of the invention. The nucleic acid sequence can be a heterologous sequence.

In another aspect, the invention is a transgenic mammal having introduced into its genome a nucleic acid sequence identified as SEQ ID NO:8, wherein the nucleic acid sequence is in addition to nucleic acid sequences which naturally occur in the DNA of the mammal. SEQ ID NO:8 includes both coding sequences (see SEQ ID NO:1) and a non-coding sequence portion, the non-coding of which is excised during the production of mRNA which contains only coding bases. Preferably, the nucleic acid sequence has been introduced into the mammal or a progenitor of the mammal by recombinant technology. Preferably, the mammal is bovine.

BRIEF DESCRIPTION OF THE DRAWINGS

FIG. 2B shows the percentage of mIgµ+ 70Z/3 cells induced by the indicated concentrations of the three stimuli.

In FIG. 4C, replicate 96 well flat bottomed plates (Costar) were seeded with $8 \times 10^4$ 70Z/3 cells in 0.1 ml of serum free medium containing the indicated concentration of RSDPLA for 2 hours at 37° C. Subsequent to this pre-incubation period, cultures were supplemented with no stimulus (_), 5 µg/ml of LPS (6), or 0.3 µg/ml of nBo-LAIT (8), as indicated in FIG. 4C. One plate was harvested 20 hours later, and cells were stained with phycoerythrin (PE) conjugated goat anti-mouse Igµg specific antibody (Southern Biotechnology). The proportion of mIgµ+ cells was assessed using a B.-D. FACScan. Illustrated are the % control responses i.e. the proportion of mIgµ+ cells observed in the presence of the indicated concentration of RSDPLA divided by the proportion of mIgµ+ cells observed in the presence of the indicated stimuli in the absence of RSDPLA (left-hand vertical axis). The second plate was pulsed with 1 µCi of $^3$H-TdR 14 hours after the addition of stimuli, harvested onto filter mats 6 hours later, and thymidine uptake assessed by liquid scintillation spectroscopy (right-hand vertical axis).

FIG. 7C shows a comparative analysis of the induction of mIg☑ expression in the murine pre-B cell line, 70Z/3, by affinity purified nBo-LAIT/sCD14 (nBo-LAIT). The 62% $(NH_4)_2SO_4$ fraction (∀) used as the starting material for molecular sieving; and fractions 47 (8), 48 (_), and 49 (6) isolated from the Superdex-75 that contained the peak content of nBo-LAIT/sCD14 as assessed by immunoblot analysis. $8 \times 10^4$ 70Z/3 cells were cultured in 0.1 ml of serum free medium in flat bottomed 96 well culture plates (Costar) for 20 hours in the presence the indicated concentrations of each of the stimuli. Cells were harvested and stained with PE conjugated goat anti-mouse Ig☑ specific antibody (Southern Biotechnology), and the proportion of mIg☑⁺ cells assessed flowcytometrically using a B.-D. FACScan.

FIG. 8A shows the sequences of the oligonucleotide probes used for detecting mRNA specific for bovine tracheal antimicrobial peptide (TAP). FIG. 8B shows the sequence of the oligonucleotide probe used to detect mRNA specific for bovine tubulin, used as a loading control.

DESCRIPTION OF PREFERRED EMBODIMENTS

Figure 1A:
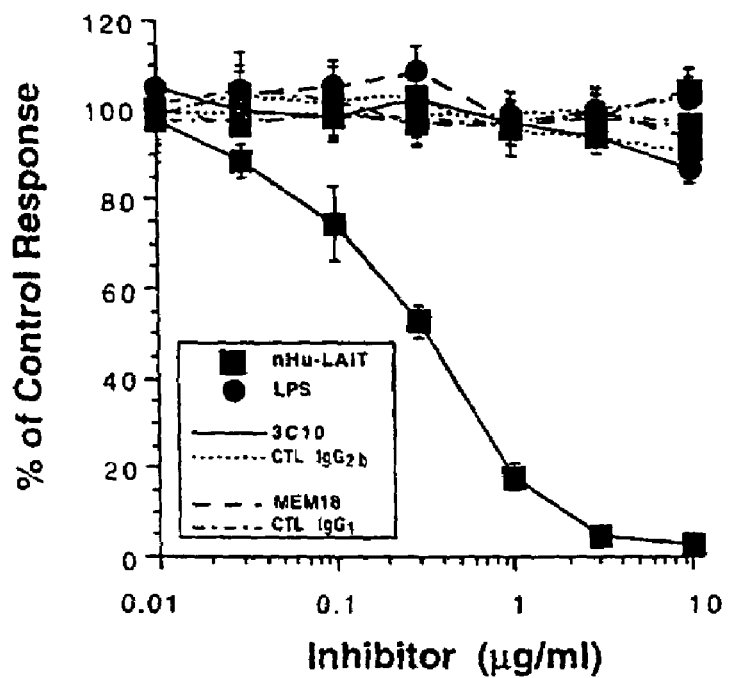
FIG. 1A shows the differential inhibition of native human LAIT (Hu-LAIT, nhCD14) mediated B cell activation by the CD14 specific mAbs 3C10 and MEM-18 (Todd S.-C. Juan, et. al. 1995. *J. Biol. Chem.* 270:5219). The indicated concentration of mAbs 3C 10 (,,), MEM-18 (,,,) or their isotype non-specific mAbs, 12CA5 (IgG2$_b$) (----) (J. Field, et. al. 1988. *Mol. Cell. Biol.* 8:2159), and W3/25 (IgG$_1$) (,-,-,) (A. F. Williams, 1977. *Cell* 12:663), respectively, was added to 0.2 ml of serum free culture medium in a 96 well flat bottomed culture plate (Costar), which contained either: 1 µg/ml of native (n) Hu-LAIT (8) or 5 µg/ml LPS (6). Following 5 hours of incubation at 37° C., 1.5×10$^5$ high buoyant density mouse splenic B cells, isolated as previously described (Ratcliffe, M. J. et. al. 1983. *J. Immunol.* 131:581), were added to each of the culture wells. At 40 hours, cultures were pulsed with 1 µCi of $^3$H-TdR, harvested onto filter mats 6 hours later, and thymidine uptake assessed by scintillation spectroscopy. Results are expressed as a percentage of the response induced by each of the two stimuli in the absence of any mAbs. The background response in the absence of stimulus ranged from 0.7 to 1.7×10$^3$ cpm; the responses to 5 µg/ml LPS and 1 µg/ml nHu-LAITin the absence of mAbs were 77.8×10$^3$ cpm, and 82.3×10$^3$ cpm, respectively. The error bars indicate one standard deviation about the mean of triplicate cultures.

The experiments described below demonstrate that the induction of high buoyant density splenic B cells derived from mouse are induced to enter and progress through cell cycle in response to recombinant forms of bovine and human LAIT-protein/sCD14, in vitro, in defined serum free medium. It is shown that a mAb 3C 10, specific for the amino terminal residues 7-14 of human CD14, but not mAb MEM-18, specific for the residues 57-65, specifically inhibits the growth promoting activity of recombinant and native bovine and human LAIT-protein/sCD 14 for mouse B cells in this assay.

In vitro induction of the differentiation of the mCD14⁻, mIg⁻ murine pre-B cell line 70Z/3 to an mIg⁺ state, by recombinant bovine and human LAIT-protein/sCD14, in defined serum free medium, is demonstrated. It is shown that this process is inhibited by mAb 3C10, but not mAb MEM-18.

It is shown that both LPS and recombinant bovine LAIT-protein/sCD14 mediated induction of the murine pre-B cell line 70Z/3 to an mIg⁺ state are inhibited by diphosphoryl lipid A derived from *Rhodopseudomonas sphaeroides* (RSDPLA).

It is shown that the colostrum of human subjects contains 100-400-fold higher concentrations of native human LAIT-protein/sCD14 compared to serum samples from the same subjects taken at the same time post-partum. It is shown that the increased concentration of human LAIT-protein/sCD14 in colostrum and milk relative to that observed in serum persists up to 400 days post-partum.

It is shown that the biological activity of native bovine LAIT-protein/sCD14 in milk obtained up to 200 days post-partum is comparable to that observed in bovine colostrum. Bovine milk-derived LAIT-protein/sCD14 is shown to induce high buoyant density splenic B cells derived from mouse to enter and progress through cell cycle, in vitro, in defined serum free medium, with specific activity comparable to that observed for colostral derived native bovine LAIT-protein/sCD14.

It is shown that B cell growth promoting activity of affinity purified nBo-LAIT is severely reduced after boiling at 99.9° C. for 10 minutes.

It is shown that sequential salting out of proteins from clarified bovine milk whey using $(NH_4)_2SO_4$ as described in detail below, results in the enrichment of native bovine LAIT-protein/sCD14 in the 62% $(NH_4)_2SO_4$ fraction. This 62% $(NH_4)_2SO_4$ fraction of bovine milk whey is shown to stimulate the induction of the differentiation of the mCD14$^-$, mIg$^-$ murine pre-B cell line 70Z/3 to an mIg$^+$ state in vitro.

It is shown that molecular sieving of proteins in the 62% $(NH_4)_2SO_4$ fraction of bovine milk whey yields fractions enriched in bioactive native bovine LAIT-protein/sCD14. These enriched fractions are shown to have roughly 100-fold higher specific activity than the 62% $(NH_4)_2SO_4$ fraction of the bovine milk in the induction of the differentiation of the mCD14$^+$, mIg$^-$ murine pre-B cell line 70Z/3 to an mIg$^+$ state in vitro.

It is shown that LPS, native forms of both bovine and human LAIT-protein/sCD14, and recombinant forms of bovine LAIT-protein/sCD14 produced in mammalian and baculovirus expression systems, each induce the expression of tracheal antimicrobial peptide (TAP) in primary bovine tracheal epithelial cells.

Experiments

LAIT-Protein/sCD14 Mediated B Cell Activation is Inhibited by MAb 3C10

The CD 14 specific mAbs, 3C 10 and MEM-18 inhibit the activation of monocytes, and their ensuing production of inflammatory cytokines mediated by LPS-LBP complexes. Further, mAb 3C10 has been shown to inhibit sCD14 mediated activation of monocytes. The latter result is consistent with the existence of receptors for sCD14 on monocytes, and that the region of sCD14 which interacts with these putative receptors is the same as or very close to that region of mCD14 on monocytes that interacts with complexes of LPS-LBP. Since monocytes are mCD14$^+$, 3C10 mediated inhibition of sCD14 function could be due to its interaction with sCD14, mCD14 expressed on the target monocytes, or both.

Figure 1B:
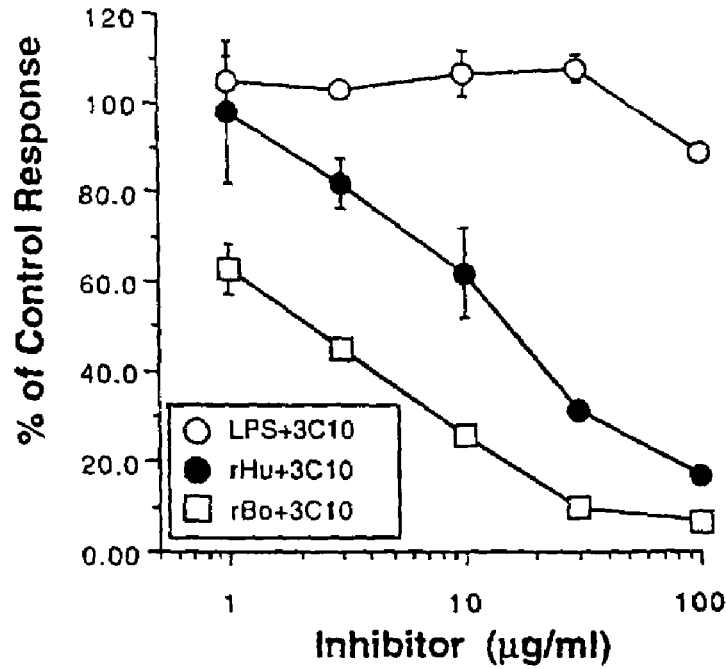
FIG. 1B shows the inhibition of recombinant (r) Hu- and rBo-LAIT mediated B cell activation by the CD14 specific mAb, 3C10. The indicated concentration of mAb 3C10, or an IgG2$_b$ isotype non-specific, mAb OX40 (Paterson, D. J. et. al. 1987. *Mol. Immunol.* 24:1281), was added to 0.2 ml of serum free culture medium in a 96 well flat bottomed culture plate (Costar), which contained either: 15 µg/ml of soluble recombinant human CD14 (rHu-LAIT) (6); 2 µg/ml soluble recombinant bovine CD14 (rBo-LAIT) (0), or 5 µg/ml LPS (/). Following a 5 hour incubation at 37° C., 1.5×10$^5$ high buoyant density splenic B cells, isolated as previously described (Ratcliffe, M. J. et. al. 1983. *J. Immunol.* 131:581), were added to each of the culture wells. At 40 hours, cultures were pulsed with 1 µCi of $^3$H-TdR, harvested onto filter mats 6 hours later, and thymidine uptake assessed by scintillation spectroscopy. Results are expressed as a percent of the response induced by each of the three stimuli in the absence of any mAb. The background response in the absence of stimulus ranged from 0.7 to 1.7×10$^3$ cpm; the responses to 5 µg/ml LPS, 15 µg/ml rHu-LAIT, and 2 µg/ml rBo-LAIT, in the absence of mAb 3C10, were 77.8×10$^3$ cpm, 10.9×10 cpm, and 82.3×10$^3$ cpm, respectively, with a standard deviation among replicate cultures of <10%. The inhibition mediated by OX40 was less than 15% at all of the concentrations tested.

The results illustrated in FIG. 1A show the differential capacity of CD14 specific mAbs to inhibit murine B cell activation mediated by native human LAIT-protein/sCD14. MAb 3C10, but not mAb MEM-18, nor their respective isotype control mAbs, inhibits the induction of B cell growth by LAIT-protein, while none of the mAbs inhibits LPS induced B cell growth. The results illustrated in FIG. 1B show that the CD14 specific mAb 3C10 inhibits both rBo-LAIT/sCD14 and rHu-LAIT/sCD14 mediated murine B cells growth, while not affecting LPS induced B cell growth.

Since the expression of mCD14 by B cells is unsettled, these results do not distinguish among possible mechanisms underlying mAb 3C10 inhibition of sCD14 mediated B cell activation. Further, while the purity of the high buoyant density murine B cells used as targets in this experiment range from 88% to 95%, the contaminating cells are mCD14$^+$. Specifically, it has been demonstrated that these B cell populations contain mRNA encoding CD14 (PCT Application No.PCT/CA97/00880). Two experiments were carried out in an attempt to clarify the mechanism(s) underlying LAIT/sCD14 mediated B cell activation.

B cells were isolated based on their expression of mIg☑by fluorescent activated cell sorting to greater than 99% purity. This population of B cells was shown to be negative for contained CD14 specific mRNA as assessed by northern blot analysis. It was subsequently demonstrated that this "CD114" B cell population responded as robustly to native Bo-LAIT/sCD14 (nBo-LAIT) derived from colostrum as did B cells not purified by this technique. Thus, by this criterion, it appears that nBo-LAIT interacts with a putative receptor on B cells, in a mCD14 independent fashion (PCT Application No. PCT/CA97/00880). The second approach used to determine the involvement of mCD14 in LAIT-protein mediated B cell activation involved assessing its ability to induce the differentiation of the CD14$^-$ pre-B cell line, 70Z/3.

LAIT/sCD14 Induces the Differentiation of a mCD14$^-$ Pre-B-Cell Line

Figure 2A:
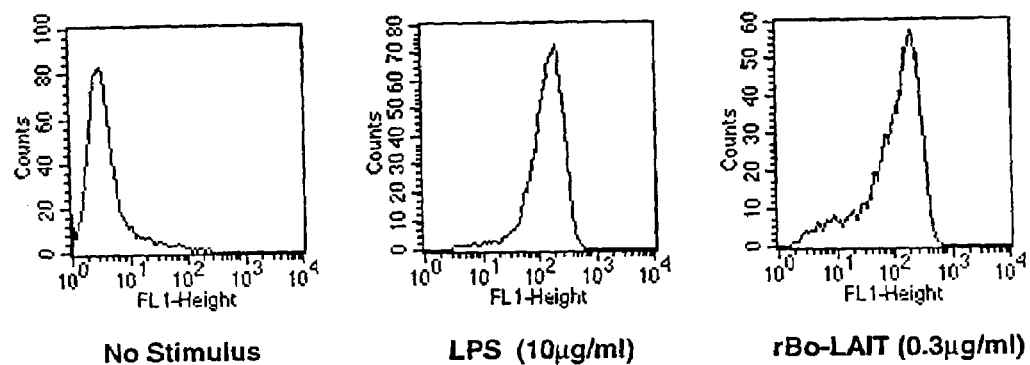
FIGS. 2A and 2B illustrate a comparative analysis of LPS and rBo-LAIT induction of membrane Igµ E expression (mIgµ) in the murine pre-B cell line, 70Z/3. 8×10$^4$ 70Z/3 cells were cultu 0.1 ml of serum free medium in flat bottomed 96 well culture plates (Costar) for 20 hours in the presence of no stimulus, or the indicated concentrations of rBo-LAIT (O), LPS derived from *S. typhimurium* (Sigma) (/), or deep rough LPS derived from *E. coli* mutant D31m4 (6) (Kirkland, T. N. , Qureshi, N. and K. Takayama 1991. *Inf and Imm.* 59:131). Cells were harvested and stained with fluorescein conjugated mAb 187.1($^F$187.1) (Yelton, D. E. et. al. 1981. *Hybridoma* 7:5), specific for murine Igµ, and the proportion of mIgµ$^+$cells assessed flowcytometrically using a B.-D. FACScan. The three upper histograms of FIG. 2A illustrate the proportions of mIgµ$^+$ 70Z/3 cells after the 20 hour culture period at 37° C.: in the stimulus (left), in the presence of 3 µg/ml *S. typhimurium* LPS (middle), and in the presence of 0.1 µg/ml rBo-LAIT (right).
Figure 2B:
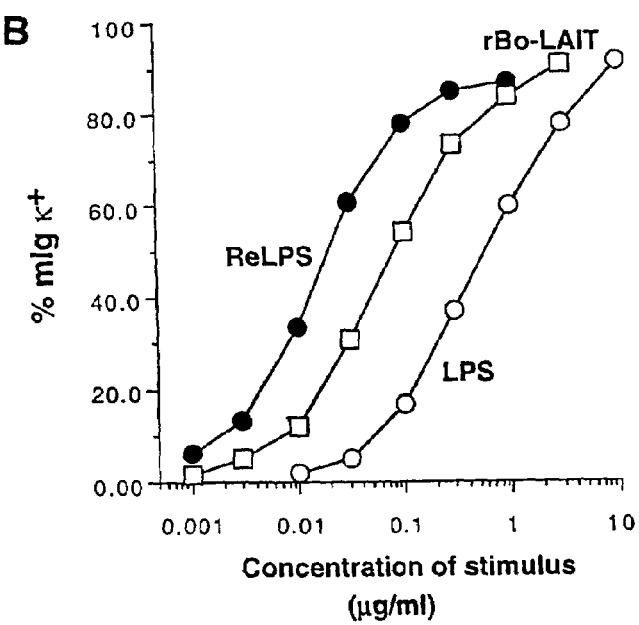

The membrane immunoglobulin negative (mIg$^-$) murine pre-B cell line 70Z/3 (Paige, C. J. et. al. 1978. *J. Immunol.* 121:641), does not express detectable mCD14 by immunofluoresence, and is negative for mRNA encoding CD14 as assessed by both northern blot analysis, and RT-PCR (Filipp, D. and M. Julius unpublished observation; Lee, J. D. et. al. 1992. *J. Exp. Med.* 175:1697). 70Z/3 is induced to a mIg☑$^+$ state upon stimulation with either LPS or IFN-β (Paige, C. J. et. al. 1978. *J. Immunol.* 121:641). The results illustrated in FIG. 2 show that rBo-LAIT/sCD14 induces the differentiation of 70Z/3 to an mIg☑$^+$ state as efficiently as does LPS. This result indicates that there is a receptor for rBo-LAIT on 70Z/3 cells, and further, that the receptor cannot be mCD14. This approach therefore provides a means by which to assess the mCD14 dependence of mAb 3C10 mediated inhibition of LAIT/sCD14 biological activity.

LAIT/sCD14 Induction of 70Z/3 Differentiation is Inhibited by mAb 3C10

Figure 3A:
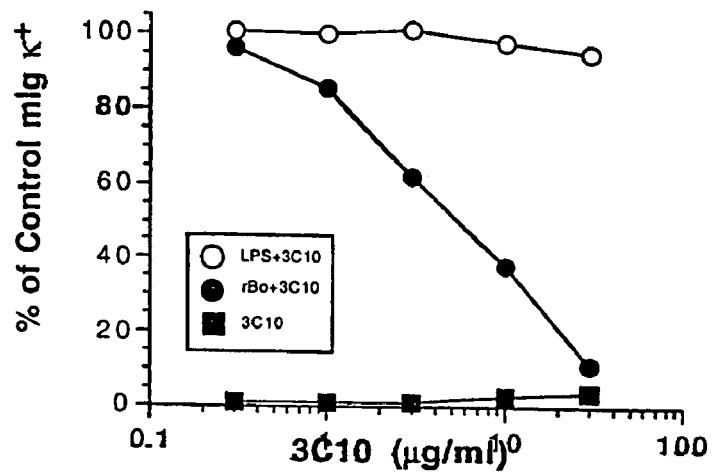
FIG. 3A shows the inhibition of rBo-LAIT mediated induction of mIgµ+ 70Z/3 cells by mAb 3C10. The indicated concentration of mAb 3C10 was added to 0.1 ml of serum free medium containing no additional stimulus (8), 3 µg/ml of *S. typhimurium* LPS (/), or 0.1 µg/ml rBo-LAIT (6) the mixtures plated in 96 well plate (Costar) and incubated at 37° C. for 2 hours. Subsequent to this pre-incubation period, $8 \times 10^4$ 70Z/3 cells were added to each of the culture wells, followed by a 20 hour culture period at 37° C., after which the cells were harvested and stained with $^F$187.1, and the proportion of mIgµ+ cells assessed flowcytometrically using a B.-D. FACScan. Illustrated are the % Control responses, i.e. the proportion of mIgµ+ 70Z/3 cells observed in the presence of the indicated concentration of mAb 3C10 divided by the proportion of mIgµ+ 70Z/3 cells observed in the absence of mAb 3C10 for each of rBo-LAI and LPS inductions. Isotype non-specific mAb OX40 did not mediate greater than 15% inhibition when cultured at any of the concentrations at which mAb 3C10 was used for either of the two stimuli.

The results illustrated in FIG. 3A show that mAb 3C10 inhibits LAIT/sCD14 induction of mIg☑expression on 70Z/3. LPS mediated induction of mIg☑ is not inhibited by mAb 3C10, illustratin that the inhibition is specific to LAIT/sCD14 mediated induction, and further that the mechanism underlying mAb 3C10 mediated inhibition does not involve its direct interaction with 70Z/3.

Figure 3B:
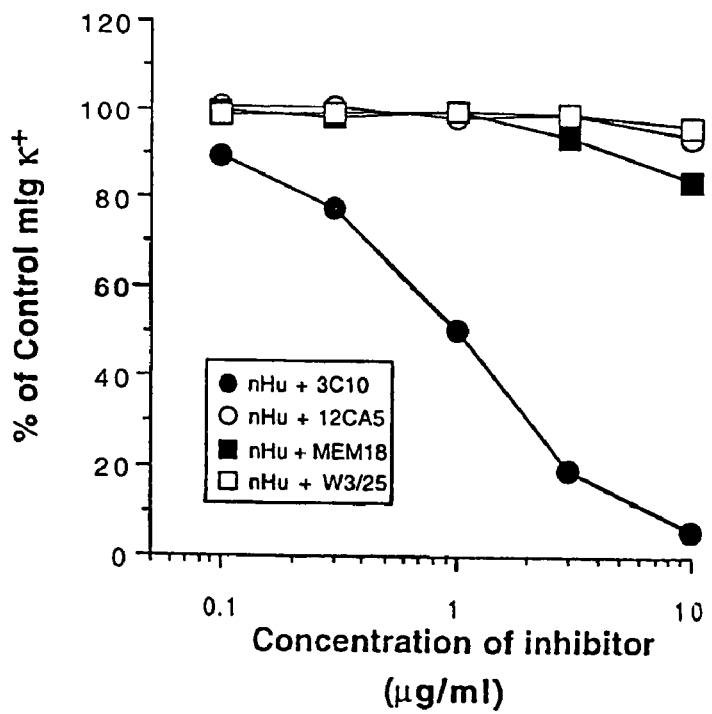
FIG. 3B shows the differential inhibition of rHu-LAIT mediated induction of mIgµ1+70Z/3 cells by CD14 specific mAbs. The indicated concentration of mAbs 3C10 (6), MEM-18 (8), or their respective isotype non-specific mAbs, 12CA5 (/) and W3/25(0), were added to 0.1 ml of serum free medium containing 0.75 µg/ml nHu-LAIT. Following a 2 hour incubation at 37° C., $8 \times 10^4$ 70Z/3 cells each of the culture wells, followed by a 20 hour culture period at 37° C., after which the cells were harvested and stained with $^F$187.1, and the proportion of mIgµ+ cells assessed flowcytometrically using a B.-D. FACScan. Illustrated are the % Control responses, i.e. the proportion of mIgµ E+70Z/3 cells observed in the presence of the indicated concentration of mAbs divided by the proportion of mIgµ+ 70Z/3 cells observed in the presence of 0.75 µg/ml nHu-LAIT in the absence of any mAb.

The results illustrated in FIG. 3B show that not all CD14 specific mAbs inhibit LAIT-protein/sCD14 mediated 70Z/3 differentiation to a mIg☑$^+$ state. Specifically, mAb 3C10, but not mAb MEM-18, also specific for CD14, nor either of their respective isotype control mAbs, inhibits the induction of 70Z/3 differentiation by recombinant human LAIT-protein/sCD14. The results indicate that mAb 3C10 interacts with LAIT/sCD14 and masks determinants which interact with the putative receptor(s) for LAIT/sCD14 expressed by 70Z/3.

Endotoxin and LAIT-Protein/sCD14 Share Signaling Pathways

As discussed in the background section, a number of models have been proposed to explain the mechanism through which LPS induces monocyte activation, and their subsequent production of pro-inflammatory cytokines. The role of mCD14, functioning as a putative receptor for endotoxin, is central to most postulated mechanisms. While the expression of mCD14 reduces the concentration of LPS required to induce cellular activation by orders of magnitude, it does not predicate LPS mediated activation. Particularly, the concentration of LPS required to induce mIg expression in mCD14⁻ 70Z/3 is higher than that required to stimulate cytokine production by mCD14⁺ monocytes (Lee, J. D. et. al. 1992. *J. Exp. Med.* 175:1697). Further, when 70Z/3 is transfected with cDNA encoding human CD14, it was demonstrated that the concentration of LPS required to induce mIg expression by mCD14+clones was 10,000-fold lower than that required in the wild-type mCD14⁻ parental line of 70Z/3. Further, the efficacy of stimulation by LPS in these circumstances was serum dependent, reflecting the involvement of LBP (Lee, J. D. et. al. 1992. *J. Exp. Med.* 175:1697). Thus, while emphasizing the central role of mCD14 in mediating cellular interaction with LPS-LBP complexes, the results also demonstrate that there is an mCD14 independent activation pathway utilized by LPS, which is serum, and thus LBP, independent.

Figure 4A:
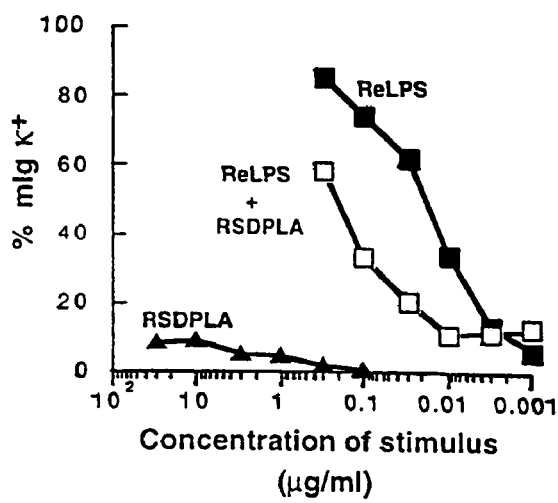
FIGS. 4A to 4C show the effect on induction of mIgµ+ in 70Z/3 cells by nBo-LAIT or by LPS of diphosphoryl lipid A derived from *Rhodopseudomonas sphaeroides* (RSDPLA). $8 \times 10^4$ 70Z/3 cells were cultured in 0.1 ml of serum free medium containing 10 µg/ml RSDPLA in 96 well plates (Costar), at 37° C. for 2 hours. Subsequent to this pre-incubation period, the indicated concentration of ReLPS (0, FIG. 4A), or native Bo-LAIT (/, FIG. 4B) was added, followed by a 20 hour culture period at 37° C. The cells were harvested and stained with $^F$187.1, and the proportion of mIgµ+ cells was assessed flowcytometrically using a B.-D. FACScan. Two controls were run for comparison to results obtain with each stimulus. RSDLPA (_) was added at the concentration indicated to cells which had been similarly pre-treated with RSDPLA. ReLPS was added to cells that had been similarly pre-incubated but with no RSDLPA (8, FIG. 4A). n-Bo-LAIT was also added to cells that had been similarly pre-incubated with no RSDLPA (6, FIG. 4B).
Figure 4B:
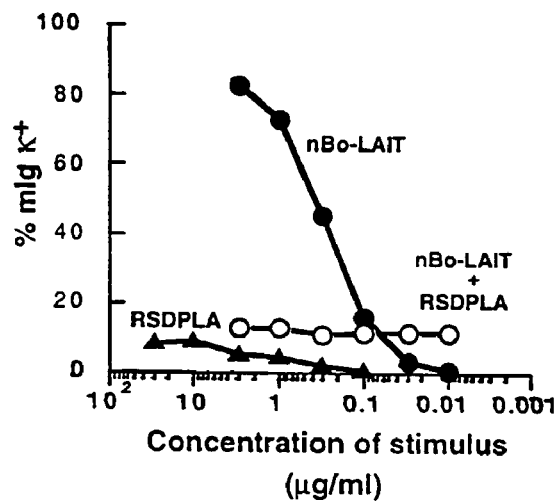
Figure 4C:
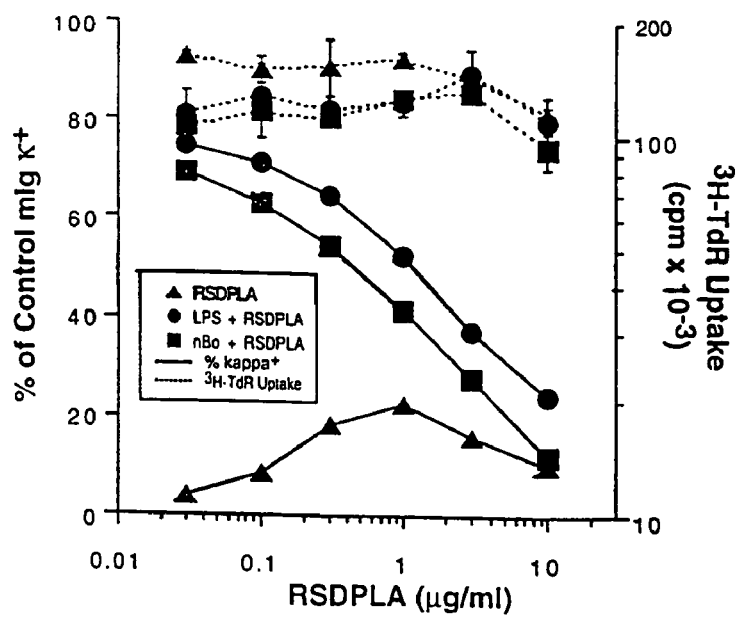

The question follows as to whether mCD14 independent pathways involved in LPS and LAIT/sCD14 activation of 70Z/3 share signalling elements. The results shown in FIG. 4 indicate that this might be the case. It has previously been demonstrated that diphosphoryl lipid A derived from LPS inhibits the activation of 70Z/3 by LPS (Kirkland, T. N., Quershi, N. and Takayama, K. 1991. Infection and Immunity 59:131). In particular, pre-incubation of 70Z/3 with diphosphoryl lipid A (RSDPLA) inhibited subsequent LPS induced expression of mIg. As shown in FIG. 4A, pre-incubation of 70Z/3 in medium containing RSDPLA at 10 ☒g/ml resulted in a 3-4-fold inhibition of LPS mediated Ig☑expression. Also shown in FIG. 4A is that RSDPLA by itself does not induce Ig☑expression on 70Z/3 over the concentration range tested, i.e., 0.1 to 30 ☒g/ml. FIG. 4B illustrates that preincubation of 70Z/3 in medium containing 10 ☒g/ml RSDPLA not only inhibits nBo-LAIT induction of Ig☑ expression, but does so with far greater efficacy than when using LPS as stimulus, resulting in at least a 10-fold inhibition of nBo-LAIT mediated induction over the entire concentration range of nBo-LAIT tested. Illustrated in FIG. 4C is that while RSDPLA inhibits both LPS and nBo-LAIT/sCD14 induction of mIg☑ expression by 70Z/3, it does not inhibit the growth of 70Z/3 at any of the concentrations tested, i.e. 0.03 ☒g/ml to 10 ☒g/ml.

RSDPLA mediated inhibition of LPS mediated activation is isologous in that the former is derived from LPS, and inhibition by RSDPLA is thought to be due to competitive binding to physiological lipid A receptor(s) expressed by 70Z/3. The ability of RSDPLA to inhibit LAIT/sCD14 mediated activation could indicate that LAIT/sCD14 and LPS share common receptor elements, and/or it could be due to RSDPLA interacting with the previously characterized LPS interaction sequence on CD14, residues 57-64 (Juan, T. S.-C. et. al. 1995. *J. Biol. Chem.* 270:5219), which in turn might inhibit LAIT/sCD14 activity in these assays, notwithstanding the LPS independence of LAIT/sCD14 function.

Figure 5A:
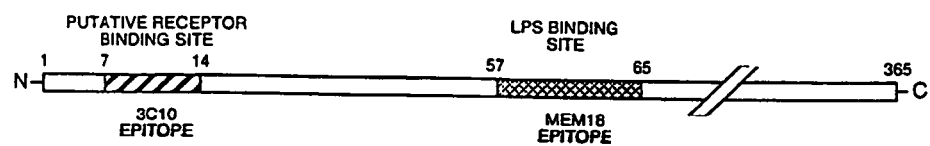
FIG. 5A is a diagrammatic representation of nHu-LAIT/CD14. Depicted are the two regions which characterize the epitopes recognized by mAb 3C10 (amino acids 7 to 14) and MEM 18 (amino acids 57 to 65).
Figure 5B:
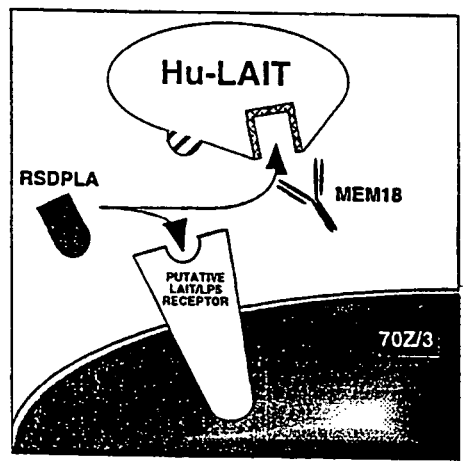
FIG. 5B is a schematic of how RSDPLA may function to inhibit Hu-LAIT mediated 70Z/3 differentiation. RSDPLA may be interacting with the LPS binding site of the Hu-LAIT protein, or RSDPLA may be interacting with the putative receptor for LAIT on the 70Z/3 cell. Some elements of LPS and LAIT-protein mediated cellular activation may be shared. Also shown is mAb MEM-18, which would block the interaction of nHu-LAIT and RSDPLA according to one of the possible modes of interaction.
Figure 5C:
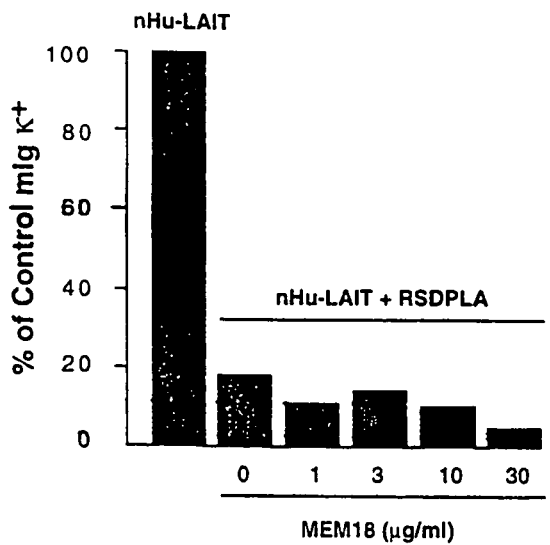
FIG. 5C shows the effect of various concentrations of mAb MEM 18 on induction of mIgµ+ in 70Z/3 cells by nHu-LAIT in the presence of RSDPLA. $8 \times 10^4$ 70Z/3 cells were cultured in 0.1 ml of serum free medium containing 30 µg/ml of RSDPLA for 2 hours at 37° C. These cultures were supplemented with 0.75 µg/ml of nHu-LAIT that had been pre-incubated with the indicated concentration of mAb MEM-18 for 2 hours at 37° C. After a further 20 hour incubation at 37° C., the cells were harvested and stained with phycoerythrin (PE) conjugated goat anti-mouse Igµ specific antibody (Southern Biotechnology). The proportion of mIgµ+ cells was assessed using a B.-D. FACScan. Illustrated are the % control responses i.e. the proportion of mIgµ+ cells observed in the presence of the indicated concentration of RSDPLA divided by the proportion of mIgµ+ cells observed (90%) in the presence of 0.75 µg/ml of nHu-LAIT in the absence of RSDPLA.

The possibility that RSDPLA inhibits LAIT-protein/sCD14 function by directly binding LAIT-protein/sCD14 was assessed as illustrated in FIG. 5. FIG. 5A shows a schematic of LAIT-protein/sCD14 and highlights the two regions of the molecule that characterize the binding sites of mAbs 3C10 and MEM-18. MEM-18 has been shown to block the binding of CD14 with LPS, and hence residues 57-65 are indicated as the LPS binding site on CD14. FIG. 5B illustrates the two potential mechanisms that could underlie RSDPLA mediated inhibition of LAIT-protein/sCD14 function. Either RSDPLA interacts directly with putative receptor elements shared by LPS and LAIT-protein/sCD14, or it may interact directly bind LAIT-protein/sCD14. If the latter were the case, then blocking the interaction of RSDPLA with LAIT-protein/sCD14 using mAb MEM-18 (FIG. 5B) should interfere with RSDPLA inhibition of LAIT-protein/sCD14 function. As shown in FIG. 5C pre-incubation of native human LAIT-protein/sCD14 with mAb MEM-18 did not alter the capacity of RSDPLA to inhibit LAIT-protein induction of mIg☑ expression by 70Z/3.

It has been demonstrated here that mAb 3C10, but not mAb MEM-18 inhibits the function of LAIT/sCD14 on both mature murine B cells (FIG. 1A) and on the murine pre-B cell line 70Z/3 (FIGS. 3A and 3B). As previously described, mAb 3C10 recognizes a sequence on CD14, residues 7 to 14, which is essential for LPS mediated signalling, but not LPS binding (Juan, T. S.-C. et. al. 1995. *J. Biol. Chem.* 270:17237). Since mAb 3C10 inhibits LPS independent LAIT/sCD14 signalling, it suggests that residues 7 to 14 on LAIT/sCD14 are involved in the interaction of this ligand with putative membrane receptor(s) structures. Further, it has been demonstrated that mAb MEM-18, that is specific for the sequence on CD14 involved in LPS binding, and is able to block LPS-CD14 interaction, has no affect on RSDPLA mediated inhibition of LAIT-protein/sCD14 activation. Thus, although not definitively shown, the interpretation that RSDPLA blocks LAIT/sCD14 signalling as a consequence of competitively competing for common receptor elements, is favoured.

LAIT/sCD14 is Enriched in Human Colostrum and Milk

Figure 6A:
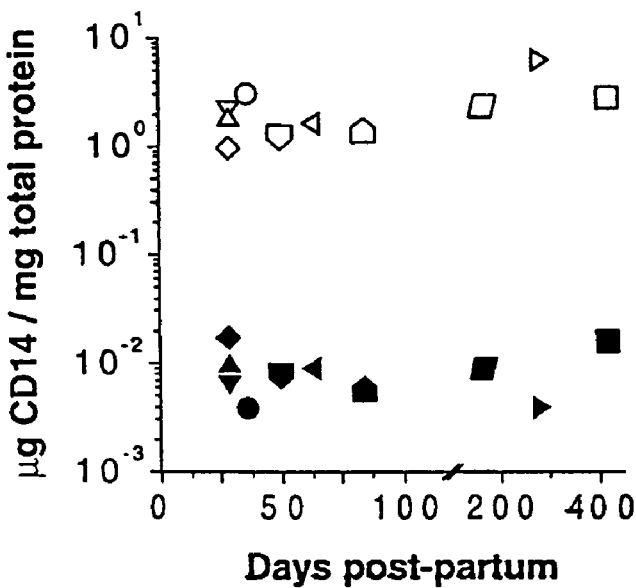
FIG. 6A shows the quantification of nHu-LAIT/sCD14 in paired samples of human milk and serum obtained from 9 subjects at the indicated time post partum. sCD14 was quantified using a commercially available ELISA kit (IBL, Hamburg). Results are presented as the ratio of sCD14/total protein in milk (open symbols) and serum (closed symbols), each shape of symbol representing a different subject. Total protein was determined using a colorimetric detection system (BiORad).

Given the possible importance of the role of soluble Hu-LAIT to newborn infants, the pattern of expression of Hu-LAIT in human females after giving birth was examined. Colostrum and milk samples were obtained from nine human subjects at various times post-partum. As it is known that serum from healthy human subjects contains between 1-5 ☒g/ml sCD14, serum samples from the aforementioned nine subjects were taken to determine whether contained sCD14 concentrations paralleled those observed in mammary secretions. CD14 was quantified using a commercially available ELISA kit, and total protein was determined using a commercially available colorimetric detection system. Results shown in FIG. 6A are presented as ☒g of CD14/mg total protein for each of the paired milk and serum samples obtained. As illustrated, human milk contains between 100-400-fold more sCD14 than does serum from the same individual. Also shown is that the enrichment of sCD14 in milk versus serum persists up to 400 days post-partum.

Heat Lability of Affinity-purified nBo-LAIT

Figure 6B:
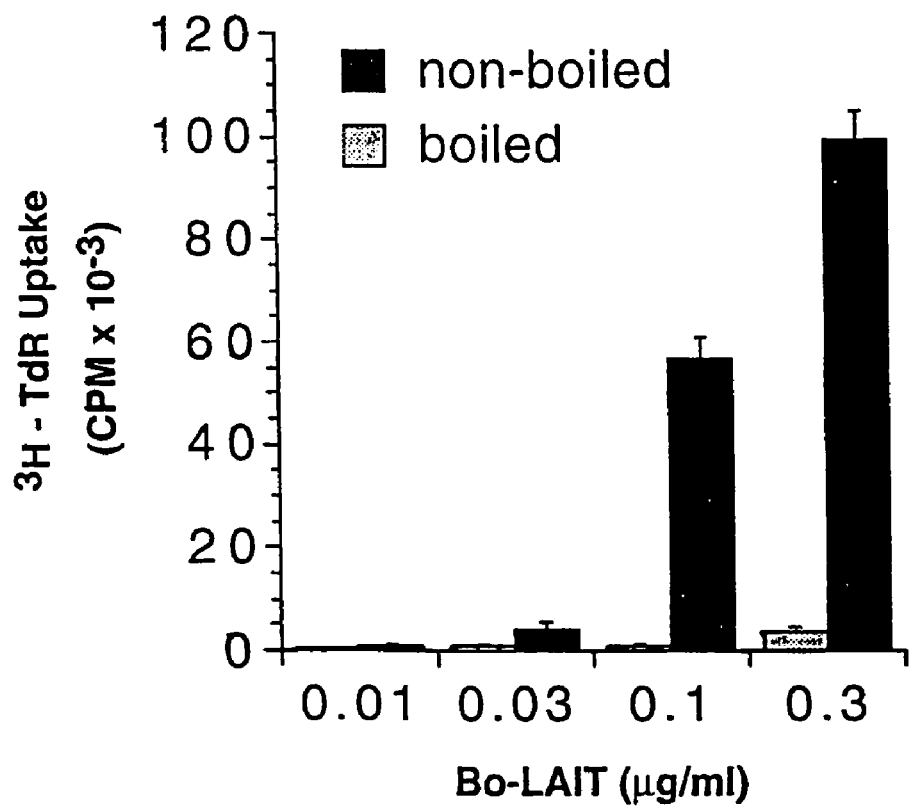
FIG. 6B shows an analysis of B cell growth promoting activity of heat denatured nBo-LAIT. $1.5 \times 10^5$ high buoyant density mouse splenic B cells from conventional C57B1/6 mice were prepared as previously described (Ratcliffe, M. J. H. and Julius, M. H. 1983. J. Immunol 131:581) and cultured in 0.2 ml of serum free medium in the presence of the indicated concentrations of stimulus. The indicated concentrations of nBo-LAIT were achieved by diluting a 10× solution which had been subjected to 99.9° C. for 10 minutes in a Perkin Elmer GeneAmp PCR system 9600, or left untreated. Subsequent to this treatment, samples were cooled on ice for 5 minutes, and added to B cell containing cultures. Cultures were pulsed with 1 µCi of $^3$H-TdR at 40 hours, harvested 6 hours later, and thymidine uptake assessed by liquid scintillation spectroscopy.

Care must be taken to avoid conditions which diminish the desired activity of CD14 or variant polypeptide of interest. FIG. 6B shows the effect of boiling affinity purified nBo-LAIT at 99° C. for 10 minutes. The large reduction in thymidine uptake by B cells indicates a dramatic reduction, if not total destruction of B cell stimulatory activity. Partial Purification of Bioactive Bovine LAIT-Protein/sCD14 from Milk; Colostrum- and Milk-Derived Bovine LAIT-protein/sCD14 have Comparable Biological Activity It was previously unknown that soluble CD14 is present in the milk of cows. In the context of this invention, the term "mammary secretion" includes colostrum and milk. "Colostrum" is a mammary secretion that begins at the time of birth of an offspring and continues for a relatively fixed period of time not usually greater than 24 hours. "Milk" is the mammary secretion which follows colostrum. A person skilled in the art can readily distinguish between the colostrum and milk. Colostrum is generally obtained during the first few hours post partum and prior to initiation of suckling. In experiments described herein, and PCT/CA 97/00880 in which bovine colostrum was used as a source of bo-LAIT, the colostrum was obtained within one hour post partum and prior to suckling.

The method previously used to isolate LAIT from bovine colostrum (PCT/CA 97/00880) was used here to obtain bo-LAIT from milk. Whole, unpasteurized cow milk was obtained from a research farm. The milk was determined to be sterile by assessing growth in liquid broth and on blood auger plates. Only aseptic material was used in the experiments described herein.

Clarified milk whey was prepared by centrifugation of colostrum first at 4420g for 30 minutes to remove cells and cellular debris. The supernatant of this spin was then centrifuged at 250,000g for two hours. The floating lipids and the pelleted casein were discarded, and the clarified colostral whey was subjected to further fractionation. Salting out of proteins contained within the milk whey preparations was accomplished using sequential precipitation in $(NH_4)_2SO_4$ by addition of a saturated solution of ammonium sulphate. The sequence of increasing salt concentrations employed was 42%: 50%: 62%: 65% (v/v) ammonium sulphate (AS). Thus, the concentration of AS in the supernatant of the material precipitated at 42% was increased to 50%; the material precipitated at 50% rescued, and the concentration of AS in the remaining supernatant increased to 62%, and so on. Each AS precipitated pellet was solubilized in 10 mM Tris-HCL pH 8.0, containing 0.15M NaCl and 1 mM AEBSF (TNAEBSF). These fractions were desalted and buffer exchanged to TNAEBSF using 10DG columns, and assayed for bioactivity.

Figure 7A:
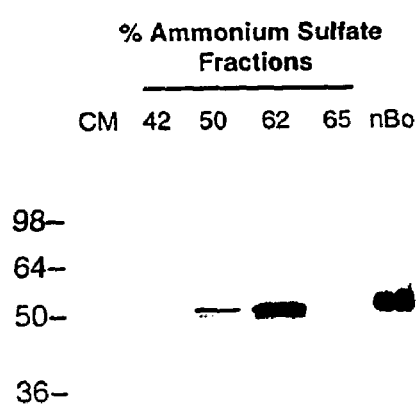
FIGS. 7A-7C show the partial purification of bioactive nBo-LAIT/CD14 using a combination of sequential salting out and size exclusion chromatography. Bovine milk whey was prepared and salted out as described in the text. Shown in FIG. 7A is the CD14 specific immunoblot of clarified milk whey (CM), affinity purified nBo-LAIT (nBo), and each of the $(NH_4)_2SO_4$ fractions tested. The immunoblot was carried out as described below for FIG. 7D. Shown in FIG. 7B is the resolution of the proteins in each of the fractions described in FIG. 7A using 10% SDS-PAGE followed by silver staining. The 62% $(NH_4)_2SO_4$ fraction containing the highest proportion of nBo-LAIT/CD14 was subjected to molecular sieving on a Superdex-75 size-exclusion FPLC column (Pharmacia) equilibrated in TN buffer (10 mM Tris pH 8.0, 150 mM NaCl). TN buffer was used to elute proteins at a flow rate of 0.4 ml/min, and 0.2 ml fractions were collected over a period of 40 minutes using an $OD_{280}$ nm detector to monitor the elution profile of protein. Each of the fractions obtained was assessed for nBo-LAIT/sCD14 by immunoblot as described for FIG. 7D. Fractions 47 to 49 from this separation procedure contained the highest concentration of nBo-LAIT/sCD14 by immunoblot analysis.
Figure 7B:
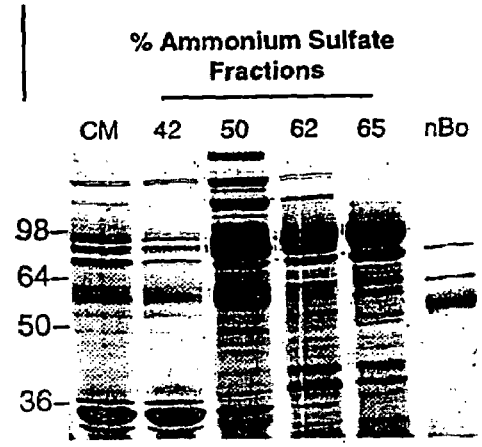

The sequential salting out of proteins from clarified bovine milk whey using $(NH_4)_2SO_4$ resulted in the enrichment of native bovine LAIT-protein/sCD14 in the 62% $(NH_4)_2SO_4$ fraction (compare FIGS. 7A and 7B). The protein concentrations in the 62% $(NH_4)_2SO_4$ fractions derived from bovine milk whey and colostral whey are 8-15 mg/ml and 47-65 mg/ml, respectively. The concentrations of LAIT-protein/sCD14 in 62% $(NH_4)_2SO_4$ fractions derived from milk and colostrum are 1-5 ☒g/ml and 5-12 respectively. Thus, LAIT-protein/sCD14 yields from these two sources is comparable at 0.15-0.26 ☒g/mg protein.

Figure 7C:
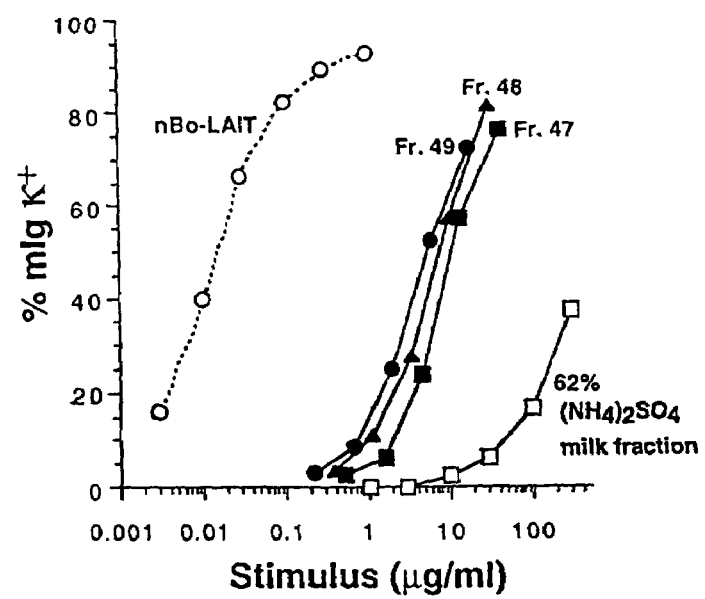

Activity of the 62% fraction was subsequently enriched. Fifty milligrams of the 62% AS enriched fraction was applied to an anion exchange column, and the material separated using a salt gradient of 50 mM to 400 mM NaCl in 10 mM Bis-tris propane, with a simultaneous pH gradient of 7.5 to 9.5. Shown in FIG. 7C is a comparative analysis of partially purified fractions of milk-derived bovine LAIT-protein/sCD14 with that of affinity purified material form the same source to induce the expression of mIg☒ in 70Z/3. As illustrated, the 62% $(NH_4)_2SO_4$ fraction had a specific activity roughly 10,000-fold lower than the affinity purified milk-derived LAIT-protein/sCD14. Also shown in FIG. 7C is the biological activity of the fractions containing the majority of LAIT-protein/sCD 14 (assessed by immunoblot analysis) obtained upon further fractionation of the 62% $(NH_4)_2SO_4$ fraction on a Sephadex 75 molecular sieving resin. The specific activity of fractions 47-49 were 100-fold higher than that of the 62% $(NH_4)_2SO_4$ fraction, and correlated with a comparable increase in LAIT-protein/sCD14 concentration.

Figure 7D:
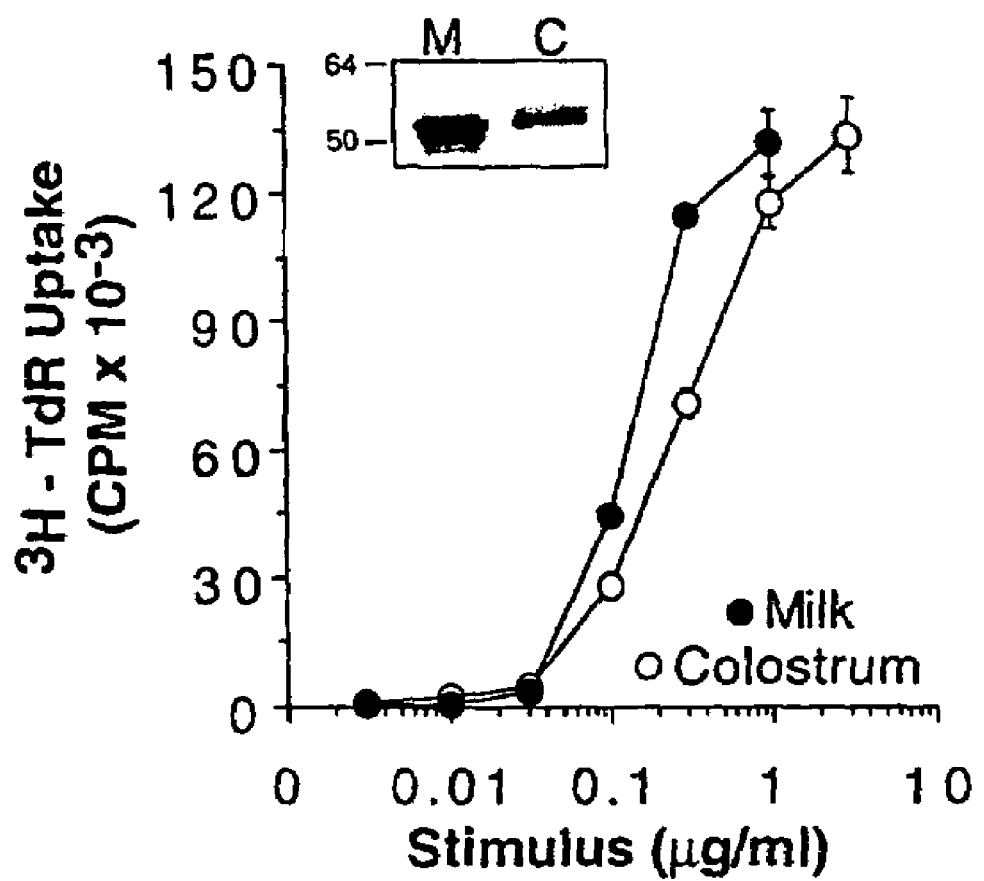
FIG. 7D shows the comparative B cell stimulatory activity of nBo-LAIT affinity purified from bovine colostrum and milk. Clarified colostral and milk whey were subjected to sequential salting out using increasing concentrations of $NH_4SO_2$ as described for FIG. 7A. The 62% $(NH_4)_2SO_4$ fraction was solubilized and desalted and sCD14 was affinity purified on mAb 3C10 conjugated to Sephadex 4B. The affinity purified material from colostrum (/), and milk (6), was added at the indicated concentrations to 0.2 ml cultures of serum free medium containing $1.5 \times 10^5$ high buoyant density splenic B cells isolated as previously described. At 40 hours, cultures were pulsed with 1 ☒Ci of ³H-TdR, harvested onto filter mats 6 hours later, and thymidine uptake assessed by scintillation spectroscopy. The insert in FIG. 7D represents an immunoblot of milk (M) and colostral (C) bovine-derived sCD14. 250 ng of protein was resolved by 10% SDS-PAGE and the protein was then transferred to a PVDF membrane. Following blocking in 5% skim milk for 1 hour, protein was revealed using a polyclonal rabbit anti-bovine CD14 in combination with horse radish peroxidase conjugated goat anti-rabbit IgG (BiORad). Signals were detected by ECL (Amersham).

Shown in FIG. 7D is a comparative analysis of milk- and colostrum-derived bovine LAIT-protein/sCD14 mediated induction of B cell growth. As illustrated, the specific activity of milk-derived material was as high as that of colostrum-derived material. The insert in FIG. 7D illustrates an immunoblot of affinity purified milk- and colostrum-derived LAIT-protein/sCD14.

It has thus been shown that LAIT-protein/sCD14 occurs naturally in bovine milk and it is possible to concentrate and to isolate the milk protein with retention of B-cell activation activity. LAIT/sCD14 Induces TAP Specific mRNA in Primary Bovine Tracheal Epithelial Cells The possibility that LPS and LAIT/sCD 14 share common receptor elements, as described above, leads to the possibility that they may have common biological activities. The possibility that LAIT/sCD14 might have a role in the induction of defensins was explored. Specific defensin molecules have been described recently in the bovines (Diamond, G. J. P. Russell, and C. L. Bevins. 1996. *PNAS* 93:5156; Schonwetter, B. S., Stolzenberg, E. D. and M. A. Zasloff. 1995. Science 267:1645). Oligonucleotide probes for bovine TAP were thus prepared for assessing the relative capacities of LPS and LAIT/sCD 14 to induce message for this antibiotic peptide in an in vitro setting.

FIG. 8A shows the sequence of the oligonucleotide probes used to detect bovine tracheal antimicrobial peptide (TAP) in primary bovine tracheal epithelial cells. TAP is a 38 amino acid polypeptide and its expression appears to be restricted to columnar epithelial cells of the bovine respiratory tract (Diamond, G. et al. 1996. *Proc. Natl. Acad. Sci. USA* 93:5156).

Figure 9A:
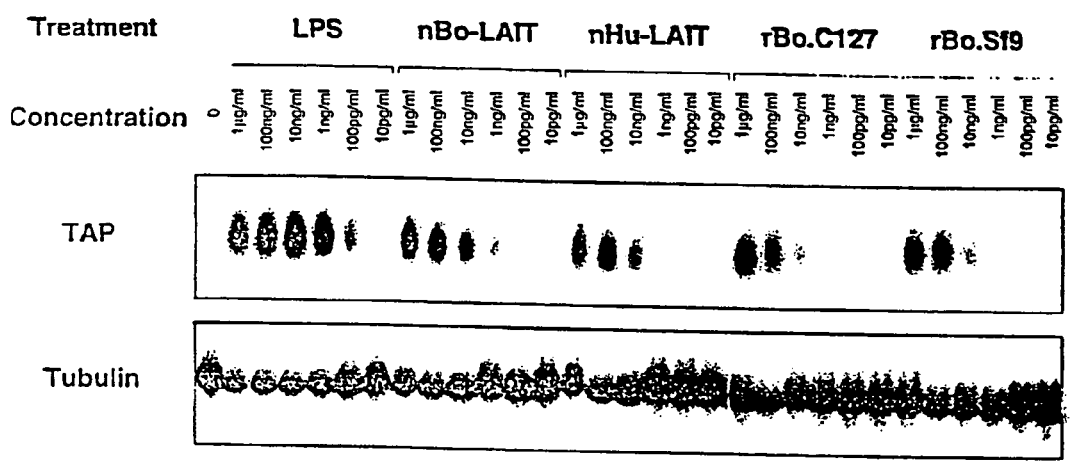
FIG. 9A shows the induction of tracheal antimicrobial peptide (TAP) mRNA in primary tracheal epithelial cells by LPS, native LAIT-protein derived from bovine (nBo-LAIT) and human (nHu-LAIT), and by recombinant bovine LAIT-protein derived from either a mammalian expression system (rBo-C127), or a baculovirus expression system (rBo-Sf9). Primary cultures of bovine tracheal epithelial cells were prepared according to previously published methods (Diamond, G. et al. 1996. *Proc. Natl. Acad. Sci. USA* 93:5156). $5 \times 10^5$ tracheal epithelial cells were cultured in 1 ml of serum free medium containing the indicated concentration of the various stimuli. After a 16 hour culture period at 37° C., total RNA from each of the cultures was isolated using the Trizol method (Gibco) and 20 ☒g loaded onto a 1.2% formaldehyde/agarose gel. Resolved RNA was then transferred to a nylon membrane (GeneScreen, DuPont) using a Vacuum blotter (Pharmacia) in 10×SSC and UV-crosslinked according to the manufacturer recommendations. 5'-end labeled TAP oligo-probes (see FIGS. 8A and 8B) were mixed 1:1 and hybridized to immobilized RNA in 50% (vol/vol) formamide/6×standard saline citrate (SSC)/5× Denhardtvs/0.5% (wt/vol) SDS/10% (wt/vol) Dextran sulfate/100 ☒g/ml Salmon sperm DNA at 42° C. for 16 to 20 hours and then washed in 2×SSC, 0.1% SDS at 65° C. for 30 minutes. Loading was normalized by assessing levels of bovine tubulin in each lane. Hybridization with bovine tubulin specific oligo-probe was done using high stringency washing conditions consisting of 0.1×SSC, 1% SDS at 65° C. for 2 hours. Signal intensities for TAP were normalized to relative RNA amount measured by assessing the signal intensity of the loading control probe using a PhosphorImager (Molecular Dynamics).

Primary bovine tracheal epithelial cells were prepared according to previously described methods (Diamond, G. et.al. 1996. *Proc. Natl. Acad. Sci. USA* 93:5156). Wells containing approximately $5 \times 10^5$ epithelial cells in 1 ml of serum free medium per well of a 24 well culture plate were prepared and stimulated for 16 hours with the indicated concentrations (FIG. 9A) of LPS, native forms of human and bovine LAIT-protein/sCD14, or recombinant forms Bo-LAIT/sCD14 prepared using either a mammalian expression system (C127) or a baculovirus expression system (Sf9). Bovine LAIT obtained from milk was used in the experiments. As illustrated in FIG. 9A, 1 ☒g/ml of either native or recombinant LAIT/sCD14, induced comparable levels of TAP specific mRNA as did 1 ☒g/ml of LPS, and resulted in a 15-20-fold increase in the signal observed in non-stimulated cells. Also shown in FIG. 9A are the signals obtained for bovine tubulin specific mRNA, which indicate that comparable amounts of RNA were loaded in each track, and which were used to normalize the TAP mRNA signals.

Figure 9B:
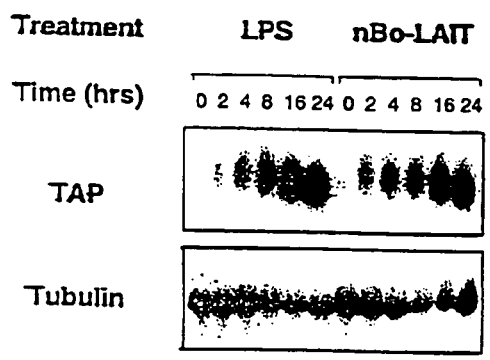
FIG. 9B shows the kinetics of LPS and nBo-LAIT/sCD14 induction of tracheal antimicrobial peptide (TAP) mRNA in primary tracheal epithelial cells. Primary tracheal epithelial cells were prepared and cultured as described in FIG. 9A. Replicate cultures all contained either 1 ☒g/ml of LPS or 1 ☒g/ml of nBo-LAIT/sCD14. At the indicated time points total RNA was isolated, resolved on agarose gels, and probed first with TAP specific oligo-probes, followed by a tubulin specific oligo probe, as described in FIG. 9A. Signal intensities for TAP were normalized to relative RNA amount measured by assessing the signal intensity of the loading control probe using a PhosphorImager (Molecular Dynamics).

Shown in FIG. 9B is a comparative analysis of the kinetics with which 1 ☒g/ml of either LPS or native bovine LAIT-protein/sCD14 induce TAP mRNA in cultures of primary bovine tracheal epithelial cells. Epithelial cells were cultures as described in FIG. 9A and the expression of TAP specific mRNA was assessed at the indicated time points. As illustrated, both stimuli induced peak expression of TAP mRNA, normalized to the level of tubulin mRNA (FIG. 9B), at 16 hours.

The present invention thus provides a method of preparing a CD14 concentrate from a mammary secretion. The secretion can be colostrum or milk or both. The secretion can be from a cow or human, or other species. For industrial processes, the production of a concentrate of endogenous bovine CD14, as it occurs naturally in cow milk, appears promising. It may be preferable under certain circumstances, to genetically modify an organism to produce CD14. This is described below.

As it is possible to diminish or destroy beneficial qualities (defensin induction activity; and/or B cell stimulation activity) of CD14 by heat treatment of milk, it may be necessary or desirable to obtain the CD14 without such prior treatment of milk. One way in which CD14 can be "concentrated" is by the salting out procedure described above. However, this is not the only method available to a person skilled in the art. For example, ion exchange chromatography, molecular sieving chromatography can be used. The methods described herein could be improved and optimized for commercial production of CD14 concentrates or isolates. Additionally, other components of milk or colostrum, that may be found to be undesirable, can be removed according to procedures known to a person skilled in the art. Examples of such procedures are described herein, in which milk is subject to centrifugation and floating lipids removed and the protein-containing liquid (whey) decanted from the casein pellet formed during centrifugation.

"Isolated" CD14 is a CD14 protein that is identified and separated from at least one contaminant with which it is ordinarily associated in nature, such as from the animal or human source of the CD14. In preferred embodiments in which the CD14 is intended for use as a medicament, the CD14 will be isolated to pharmaceutically acceptable levels of purity with respect to proteins of its species of origin. In preferred embodiments, CD14 protein will be purified (1) to greater than 95% by weight of protein as determined by the Lowry method, and most preferably more than 99% by weight. These are preferred degrees of isolation.

A CD14 "concentrate" is a CD14 protein obtained from a natural source which has been treated so as to be present in the concentrate in a greater concentration than that at which it is obtained in the natural source.

By "soluble" CD14, is meant a CD14 molecule that is not membrane bound, as by a glycosyl-phospha-tidyl-inositol anchor.

As far as treatments are concerned, it is important that the desired CD14 activity be retained in the concentrated CD14. Thus, in producing CD14 for use in activating B cells, a solution containing CD14 would not be heated above 99° C. for 10 minutes, for example, as these conditions are known to severely reduce this type of CD14 activity. See FIG. 6B in which it is demonstrated that the activity of affinity purified n-bo-LAIT is essentially destroyed under these conditions.

Using the techniques described herein, a skilled person can readily determine conditions that are harmful to a desired activity or that are relatively benign. Thus for example, the effects of various temperatures and times can be applied (e.g., 40° C., 50° C., 60° C., 70° C., etc.), could be applied to solutions containing CD14 for various lengths of time (for example, 1 minute, 2 minutes . . . 10 minutes) and the effect on B cell stimulatory activity determined according to methods disclosed herein. Likewise, the effect of such conditions on defensin induction in epithelial cells could be readily determined using a similar scheme. The effects of other conditions, say salt effects, or other chemicals that might be used in the treatment of milk could also be readily determined. Care would then be taken to avoid exposure of CD14 to conditions found to be adverse to its desirable activities.

As CD14 is concentrated, the amount or concentration of CD14 can be determined according to routine methods. A popular assay is the chemiluminescence-based ELISA assay. For detection of human CD14, commercially available kits can be utilized. (IBL, Hamburg, Germany)

For detection of bovine CD14, or any other species, an ELISA assay can readily be developed by a skilled person, an example of which assay follows. A recombinant CD14 is prepared, as described in PCT application No. PCT/CA 97/00880. The recombinant material is used to generate a standard curve. Polyclonal antibodies are generated in a rabbit against the recombinant molecule and IgG fractions isolated. The IGg is then immobilized on an ELISA plate and washed to remove the excess (non-bound) immunoglobulin. This is followed by addition of BSA (bovine serum albumin) to "block" unreacted sites on the ELISA plate. The recombinant protein is titered in over a broad range of concentrations, e.g., from 100 μg to 1 ng per ml in 10-fold increments. The plate is washed. Antibody is labelled by conjugation to an enzyme, for example, horse radish peroxidase, and this is exposed to the titered plates, incubated, and excess antibody is washed off. The bound outer antibody is revealed through the addition of enzyme substrate and developed and read on an ELISA plate reader.

A linear portion of the curve (absorbance vs protein concentration) is used as the standard as this is generally found to be a suitably sensitive range. The amount of bound antibody (as indicated through optical density) corresponds to a known concentration of the protein. To determine the concentration of protein in an unknown sample, serially diluted samples of the unknown are added to a new plate to the point where a suitable absorbance (one that falls within the range of standard curve) is found and the amount of protein present in the original unknown sample calculated.

Such an assay can be routinely developed for CD14 of any species for which a polyclonal can be obtained.

When an antibody is said to be "specific for" a polypeptide having a particular amino acid sequence (or other antigen), it is meant, as would be understood by a skilled person, that the antibody and polypeptide will bind with each other in a highly selective manner and the polypeptide will not bind with the multitude of other antibodies which may be evoked by other antigens. In such case, it can be equivalently stated that the polypeptide is "specifically recognized by" the antibody.

Once the concentration of a given CD14 concentrate is determined, provided it is free of other undesirable components, it is then useful for incorporation into medicaments, food products, etc. in desired quantities. Thus, for example, 0.1 (5)$_g$ of a concentrate containing 100 ⊠g/g of CD14 would be incorporated into a food bar which is to contain 10 (500) ⊠g of CD14.

It may be desirable to convert a liquid concentrate into a solid form, for example, by subjecting the liquid to evaporation, lyophylization, or other technique.

It may at times be desirable to include one or more preservatives to maintain the activity of the CD14, if it is to be included in a liquid, such as infant formula, for example.

There are surprisingly simple, yet powerful aspects of the present invention. For example, one aspect of the invention is a method for testing for the presence of CD14 in a composition containing protein of a mammary secretion. Such a method, although straightforward to apply, was not possible prior to the knowledge that CD14 occurs naturally in mammary secretions, particularly bovine milk. According to the method, the composition is exposed to an antibody which is specific for CD14 and it is determined whether CD14 endogenous to the secretion is present in the sample based on whether CD14-antibody complex has formed in the exposing step, using for example, an ELISA assay.

The invention also provides a method for determining the amount of endogenous CD14 contained in a composition containing protein of a mammary secretion, particularly, bovine milk. The composition is provided. The sample is exposed to an antibody which is specific for CD14 and the amount of CD14 endogenous to the secretion present in the sample based on the amount of CD14-antibody complex formed in the exposing step. Again, a suitable ELISA assay can be used.

According to these methods, human or bovine colostrum or milk can be used as the source of CD14.

In another aspect, the invention is a method for determining the suitability of a product derived from a mammary. secretion for a desired use, e.g., for use in inducing or stimulating defensin production (or B cell activation) in mammals. The method includes providing a sample of the product and determining the amount of CD14 present in the sample. Knowing the amount of CD14 in the sample, a skilled person can then incorporate an appropriate amount of the product into a composition for use, again according to the desired activity. For example, a use of human soluble CD14 (recombinant) is described in U.S. Pat. No. 5,804,189 and determining the amount of bovine CD14 that achieves comparable results would be within the capacity of a person skilled in the art.

According to certain aspects of this invention, the protein having CD14-like activity, (e.g., B cell stimulating activity, or defensin induction activity) can be naturally occurring, as in mammary secretions, or it can be manufactured according to chemical or recombinant techniques. A "recombinant" protein or polypeptide is one produced by using molecular genetic techniques to express an isolated nucleic acid sequence, as would be understood by a person skilled in the art.

In this specification, homology is calculated by standard methods which involve aligning two sequences to be compared so that maximum matching occurs, and calculating the percentage of matches. In one preferred aspect, the invention is a method of ameliorating the symptoms of sepsis comprising administering to a mammal in need thereof an effective amount of a soluble protein so as to directly expose epithelial cells of the mammal to the protein, the protein having an amino acid sequence which is at least about 63% conserved in relation to the amino acid sequence identified as SEQ ID NO:5 and having the ability to induce expression of defensins in epithelial cells. In other words, the homology of the sequence in question has at least about 63% homology with SEQ ID NO:5.

Substantially equivalent substances to these include those wherein one or more of the residues of the native sequence is deleted, substituted for, or inserted by a different amino acid or acids.

It is possible to vary the polypeptide sequences described herein while retaining at least a portion of desired activity. Preferred variations include substitutions which are conservative, i.e., ones wherein a residue is replaced by another of the same general type. As is well understood, naturally occurring amino acids can be subclassified as acidic, basic, neutral and polar, or neutral and nonpolar. It will of course be understood, without the intention of being limited thereby, that a variety of substitutions of amino acids is possible while "preserving" the structure responsible for the bone stimulatory effect of the polypeptides disclosed herein. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, cysteine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. These sorts of substitutions and interchanges are well known to those skilled in the art, as exemplified by U.S. Pat. No. 5,487,983. Guidance in determining which amino acid residues may be substituted, inserted, or deleted without abolishing biological or immunological activity may be found using computer programs well known in the art, for example, DNASTAR software.

"Sequence identity or homology" thus refers to the sequence similarity between two polypeptide molecules or between two nucleic acid molecules. When a position in both of the two compared polypeptide sequences, for example, is occupied by the same amino acid (for example, if a position in each of two polypeptide molecules is an alanine residue, then the molecules are homologous or sequences are identical at that position. The percent of homology between two molecules or sequence identity between two sequences is a function of the number of such matching positions shared by the two sequences divided by the number of positions compared× 100. For example, if 6 of 10, of the positions in two sequences are the same then the two sequences are 60% homologous or have 60% sequence identity. By way of example, the polypeptide sequences METLIA and MPTWIF share 50% homology or sequence identity. Generally, a comparison is made when two sequences are aligned to give maximum homology.

The comparison of sequences and determination of percent homology between two sequences can be accomplished using a mathematical algorithm. In this specification, the alignment can be performed according to the Clustal method.

The Clustal algorithm (as applied here using software available from DNASTAR Inc., 1228 South Park Street, Madison, Wis., USA, 1994) is recommended for aligning sequences whose similarity might not necessarily be evolutionary. The algorithm is described by Higgins, D. G. et al. 1989. *CABIOS* 5:151. The same software programme provides for aligning sequences according to the Jotun Hein method, which is recommended for aligning sequences of highly evolved families that have clear evolutionary relationship. The algorithm is described by Hein, J. 1990. *Methods in Enzymology* 183:626. Programme default settings (standard parameters) are used. In the case of weighting amino acid residues based on evolutionary substitution patterns, charge, structural and chemical similarity, a percent acceptable mutation (PAM) setting of 250 is selected. For protein alignments, the pairwise alignment parameters are K-tuple=1, Gap penalty=3, Window=5, and Diagonals Saved=5 are used.

In one preferred aspect, the present invention is a method of ameliorating the symptoms of 30 sepsis comprising administering to a mammal in need thereof an effective amount of a soluble protein so as to directly expose epithelial cells of the mammal to the protein, the protein having an amino acid sequence which is at least about 63% conserved in relation to the amino acid sequence identified as SEQ ID NO:5 and having the ability to induce expression of defensins in epithelial cells. In other words, the homology of the sequence in question has at least about 63% homology with SEQ ID NO:5.

Thus the present invention also provides compositions containing an effective amount of compounds of the present invention, including the nontoxic addition salts, amides and esters thereof, which may, alone, serve to provide the treatment benefits described above. Such compositions can also be provided together with physiologically tolerable liquid, gel or solid diluents, adjuvants and excipients.

In situations involving CD14 proteins, about 250 to 300 μg of polypeptide per kg of bodyweight of mammal can be fed, as an example, to a mammal per day based on an average daily consumption of between about 18 and 36 mls of fluid per day of fluid. It will be appreciated that consumption the by very young mammals increases over time. The dosage to be administered is based on the measured sCD14 concentration in adult breast milk of 10 to 20 μg per ml, considering that a human infant increases its milk intake from about 0.1 to about 1 per day over the first six months after birth and assuming a weight ratio of about 28 between human and rat. In practice, particularly as human subjects are concerned, the daily dosage may well be from about 250 μg to about 2500 μg or more per kg of bodyweight per day. More preferably, the dosage would be in the neighborhood of from about 300 μg to about 1 mg per kg of bodyweight per day. It may be that the preferred frequency of administration would be greater or less than once per day, depending upon the route of administration, convenience, and the variation of effectiveness of treatment with frequency of and amount used per administration. The dosage administered also depends on the subject and to which effect such administration is to give. The dosage of any one or more of the compounds will depend on many factors including the specific compound or combination of compounds being utilized, the mode of administration, and the mammal being treated. Dosages of a particular compound or combination of compounds can be determined using conventional considerations; for example, by customary comparison of the differential activities of the subject compounds and that of a known agent, that is, by means of an appropriate pharmacological protocol.

Pharmaceutical preparations include any of the compounds prepared as an injectable solution, including an injectable solution prepared just prior to use. An injectable can be either a liquid solution or suspension; solid forms suitable for solution in, or suspension in, liquid prior to injection may also be prepared. The preparation may also be emulsified. The active protein is often mixed with diluents and excipients which are physiologically tolerable and compatible with the polypeptide. Suitable diluents and excipients are, for example, water, saline, dextrose, glycerol, or the like, and combinations thereof. In addition, if desired, the compositions can contain minor amounts of auxiliary substances such as wetting or emulsifying agents, stabilizing or pH buffering agents, and the like.

Pharmaceutical preparations include the employment of the compounds in admixture with conventional excipients, that is, pharmaceutically acceptable organic or inorganic carrier substances which do not deleteriously react with the compounds, and which possibly enhance the storage and handling stability of the compounds. The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

The compositions are conventionally administered parenterally, by injection, for example either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills capsules, sustained release formulations, or powders, and contain 10%-95% of active ingredient, preferably 25%-70%. Oral formulations can include formulations designed to protect the protein until it reaches the site of intended action, as appropriate.

The protein compounds may be formulated into the compositions as neutral or salt forms. Pharmaceutically acceptable non-toxic salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The compounds of the invention can be homopolymerized to themselves. The compounds can also be conjugated to biocompatible polymeric compounds such as BIOPOL™ (WR Grace & Co.-Conn.).

Methods known in the art for making formulations can be found in, for example, "Remington's Pharmaceutical Sciences."

In the case of a general health promoting regimen, a preferred route of administration would likely be oral, CD14 being present in a liquid such that the G1 tract is exposed to the CD14 upon swallowing of the liquid. It might even be contained in a chewy or malleable substance which protects the CD14 from degradation but which readily releases the CD14 upon mastication, for subsequent exposure thereof to the GI tract.

The compositions of the present invention may be topically applied to the wound site in any suitable pharmaceutically acceptable vehicle, for example, a liquid carrier such as propylene glycol ethanol, propylene glycol ethanol chloroform, and the like. A possible concentration of the active compound in these compositions is at least 0.01% by weight, more likely from about 0.1% to about 0.5% by weight and more likely still from about 0.05% to about 0.2% by weight, but any therapeutically effective concentration may be used.

The compositions of the present invention may also be formulated in any number of other ways, depending on whether an aqueous solution, cream or ointment is desired and whether it would be used/and its site of use set as on the surface of the skin or in the eye.

Compositions formulated as a cream may contain a cream stabilizer such an xanthene gum, an emulsifier preferably a non-ionic emulsifier, at least one liquid and one solid hydrophobic material selected from the liquid and solid fatty acids, fatty alcohols, fatty acid esters, pharmaceutical grades of waxes and hydrocarbons, the latter ranging from liquids through semi-liquids such as petrolatum, to solids and the likes, preservative, an antioxidant, and water.

Methods for promoting the healing of a wound by reducing infection to the skin include applying or contacting the compositions of the present invention that promote defensin production in epithelial cells directly to the wound. The composition is permitted to remain in contact with the wound for a period of time sufficient to aid in reducing infection, for example. Such methods include incorporating compositions of the present invention into a cream formulation or soaking a gauze dressing with a solution of the composition and then applying the cream or soaked gauze to a wound site such as a burn, donor site wound, ulcer or any type of cutaneous wound. Additionally, sutures or staples may be coated or soaked with a composition of the invention and used to close an open wound.

The type of wounds that may be treated using the composition of the present invention include those which result from any medical or accidental injury which causes epithelial damage such asophthalmic wounds, such as those which result from corneal ulcers, cutaneous wounds, such as burn wounds, donor site wounds from skin transplants and ulcers. Additionally, dermatological conditions in which the skin has been damaged may be treated with the compositions of the present invention. Leg and foot ulcers may also be treated with compositions of the present invention.

Administration of compositions of the present invention through the use of an aerosol would be particularly suitable for exposing the trachea and even the lungs to CD14.

In any event, the advantage of exposing bacteria (or viruses, fungi, etc.) to one or more defensins during ingestion or inhalation, etc. would be generally understood. This would be especially true in the case of subjects not necessarily capable of mounting a full or normal immune response. In the case of gram-negative bacteria, from which can be generated LPS, the presence of one or more defensins in the GI tract or trachea might be especially advantageous to those thought to be at high risk for septic shock.

In another aspect, the present invention includes a transgenic mammal, which has been genetically altered to provide for enhanced CD14 production in its milk. Though technology for producing transgenic mice has been used for two decades, the feasibility of introducing foreign genes into the genome of cattle, including goats, sheep, cows and pigs has only recently been demonstrated. Although more difficult technically, the introduction of cloned genes encoding molecules of pharmaceutical importance into livestock provides the advantage of being able to significantly scale-up the production of recombinant proteins. This in turn would dramatically lower production costs. In this way, the transgenic livestock can be considered as bioreactors', producing pharmaceutically useful proteins in the milk, blood, or urine.

Over the past few years the expression of proteins in blood and tissue has significantly expanded the potential application of transgenic animals in medicine. For example, the creation of "stealth animal organs" for use in human transplantation has recently received much attention. Importantly, significant progress has been made in the ability to express transgenic proteins in milk. Studies carried out so far have focused on directing expression of proteins to the mammary gland and improving their production level.

The technique for the production of transgenic animals follows well established principles (Marki, U. and Harri, A. 1996. *Int. J. Exp. Path.* 77:247). The gene of interest is combined with a promoter sequence that directs and regulates the expression of the gene in a tissue/cell specific fashion in the transgenic animal. The expression construct (DNA) is injected into pronuclei of fertilized ova, and the injected ova are implanted into hormonally synchronized foster mothers. The animals resulting from this artificial insemination are controlled for the integration of the injected DNA construct. The offspring of the founder animals are tested for the expression of the gene, and its product, and the inheritance pattern of the gene to ensure germ line transmission, that is, that the transgene has been incorporated into the germ line of the animal.

In a preferred aspect, the invention is a transgenic bovine mammal in which CD14 (or analog thereof which directly activates B cells, or which directly induces defensin production in epithelial cells) is introduced by recombinant DNA technology into the mammal so as to be under the control of the endogenous CD14 promoter.

In another preferred aspect, the transgenic mammal is a bovine having a genome having introduced thereinto additional copies of the genomic sequence (exon and intron, i.e., SEQ ID NO:8) from which mRNA encoding endogenous bovine CD 14 is derived.

Soluble CD14 is a natural component of colostrum and milk in the three species tested so far: human, cow and mouse. Although the molecular basis underlying the appearance of soluble CD14 in these secretions is not well understood, the role of the endogenous CD14 promoter likely plays an important role in this regard. Therefore, the use of the endogenous CD14 promoter sequence is used to drive the expression of "transgenic" CD14, as well a tissue specific promoter, which will selectively activate the expression of transgenic CD14 within mammary tissues.

The use of genomic, rather than cDNA sequences in the preparation of transgenic animals has been shown to result in a more efficient expression of the transgene (Janne, J. et. al. 1994. *Int. J. Biochem.* 26:859). Thus bovine and/or human genomic DNA encoding CD14 can be cloned in combination with the bovine CD14 endogenous promoter sequences. Alternatively, the ovine β-lactoglobulin promoter (Wright, G. et. al. 1991. *Biotechnology* 9:830) which directs and regulates the gene expression predominantly to the mammary gland. Vector carrying the gene construct can be added with efficient transcription terminators as well as with matrix attached regions and specialized chromatin sequences which serve to enhance the expression of the transgene and to insulate it from the down-regulating effect of the chromatin environment. This construct is injected into the pronucleus of an ovum from the desired species, and implanted into a hormonally synchronized recipient of that species.

Each of the citations referred to in this application are incorporated herein by reference, in its entirety. Also incorporated herein by reference, are the complete specifications and claims of U.S. Provisional Patent Application No. 60/086,884, filed May 27, 1999, from which this application claims priority and currently pending (as of the filing date of this application) U.S. patent application Ser. No. 08/746,883, filed Nov. 18, 1996.

Polypeptide and protein sequences discussed herein are identified as follows:

SEQ ID NO:1: Nucleic acid coding sequence for bovine CD14.

SEQ ID NO:2: Nucleic acid coding sequence for human CD14.

SEQ ID NO:3: Nucleic acid coding sequence for murine CD14.

SEQ ID NO:4: Amino acid sequence for bovine CD 14.

SEQ ID NO:5: Amino acid sequence for human CD14.

SEQ ID NO:6: Amino acid sequence for murine CD14.

SEQ ID NO:7: Amino acid sequence for rabbit CD14.

SEQ ID NO:8: Genomic nucleic acid sequence for bovine CD14.

In SEQ ID NO:8, bases 1 to 83 are the 5' untranslated region, 84 to 86 is the ATG start codon, 87 to 163 is an intron, bases 164 to 1282 is a coding sequence and bases 1283 to 1405 are the 3'-untranslated region.

The amino acid sequence for rabbit CD14 is previously known (Ikeda, A. et al. 1997. *J. Vet. Med. Sci.* 59:715).

The homology between human and bovine was found to be 70.8%, between human and mouse was found to be 63.4%, between human and rabbit was found to be 71.8% and between bovine and mouse was found to be 58.7%.

The invention claimed is:

1. A method of stimulating expression of at least one defensin in a mammal in need thereof, by orally administering to the mammal a masticable product comprising isolated soluble CD14 obtained from a mammalian mammary secretion, so as to directly expose the CD14 to epithelial cells of the mammal wherein the CD14 comprises an amino acid sequence selected from the group consisting of SEQ ID NO:4, SEQ ID NO:5, and SEQ ID NO:6.

2. The method of claim 1, wherein the CD14 is obtained from bovine milk.

3. The method of claim 1 wherein, if the secretion has been previously subjected to a treatment step, the treatment step is sufficiently mild to permit preservation of CD14 activity for inducing or stimulating defensin production in epithelial cells.

4. The method of claim 1, wherein said amino acid sequence is SEQ ID NO:4.

5. A method of stimulating expression of at least one defensin in a mammal in need thereof, by directly exposing a compound to epithelial cells of the mammal wherein the compound comprises isolated soluble CD14, and exposing epithelial cells of the mammal comprises exposing the respiratory tract of a said mammal to an effective amount of a said compound and includes administering the compound in the form of an aerosol wherein the CD14 comprises an amino acid sequence selected from the group consisting of SEQ ID NO:4, SEQ ID NO:5, and SEQ ID NO:6.

6. A method of stimulating expression of at least one defensin in a mammal in need thereof, by administering to the mammal a compound, wherein said compound comprises an amino acid sequence identified as SEQ ID NO:4 so as to directly expose the compound to epithelial cells of the mammal and the compound is provided as a component of masticable product.

7. The method of claim 6, wherein the protein consists essentially of the amino acid sequence identified as SEQ ID NO:4.

8. The method of claim 1, wherein the masticable product is a food bar.

9. The method of claim 8, wherein the food bar comprises chocolate.

10. The method of claim 8, wherein the food bar comprises protein in addition to the CD14.

11. The method of claim 2, wherein said amino acid sequence comprises SEQ ID NO:4.

12. The method of claim 3, wherein said amino acid sequence comprises SEQ ID NO:4.

13. The method of claim 1, wherein the masticable product is a food bar.

14. The method of claim 2, wherein the masticable product is a food bar.

15. The method of claim 3, wherein the masticable product is a food bar.

16. The method of claim 4, wherein the masticable product is a food bar.

17. The method of claim 1, wherein the food bar comprises chocolate.

18. The method of claim 3, wherein the food bar comprises chocolate.

19. The method of claim 4, wherein the food bar comprises chocolate.

20. The method of claim 1, wherein the food bar comprises protein in addition to the CD14.

21. The method of claim 3, wherein the food bar comprises protein in addition to the CD14.

22. The method of claim 4, wherein the food bar comprises protein in addition to the CD14.

* * * * *